United States Patent
Shah

(10) Patent No.: US 12,369,833 B2
(45) Date of Patent: Jul. 29, 2025

(54) MOBILE ELECTROCARDIOGRAM SYSTEM

(71) Applicant: Rakesh Shah, Newtown, PA (US)

(72) Inventor: Rakesh Shah, Newtown, PA (US)

(*) Notice: Subject to any disclaimer, the term of this patent is extended or adjusted under 35 U.S.C. 154(b) by 0 days.

(21) Appl. No.: 18/312,362

(22) Filed: May 4, 2023

(65) Prior Publication Data
US 2023/0414151 A1    Dec. 28, 2023

Related U.S. Application Data

(63) Continuation of application No. 16/293,573, filed on Mar. 5, 2019, now abandoned.
(Continued)

(51) Int. Cl.
| A61B 5/333 | (2021.01) |
| A61B 5/00 | (2006.01) |
| A61B 5/30 | (2021.01) |

(52) U.S. Cl.
CPC ............ *A61B 5/333* (2021.01); *A61B 5/0006* (2013.01); *A61B 5/303* (2021.01); *A61B 5/681* (2013.01);
(Continued)

(58) Field of Classification Search
CPC ... A61B 5/0006; A61B 5/0022; A61B 5/0402; A61B 5/04012; A61B 5/02438; A61B 5/6898; A61B 5/7264; A61B 5/0002; A61B 5/00; A61B 2562/222; A61B 5/0004; A61B 5/72; A61B 5/0245; A61B 5/04; A61B 5/04017; A61B 5/0404; A61B 5/05; A61B 5/7253; A61N 1/37247; A61N 1/025; A61N 1/37252; A61N 1/08; A61N 1/36125; G16H 40/63; G16H 50/20; G16H 40/67; G16H 10/60; G16H 50/50; G16H 80/00;
(Continued)

(56) References Cited

U.S. PATENT DOCUMENTS

| 5,339,823 A | 8/1994 | Reinhold, Jr. |
| 6,282,440 B1 | 8/2001 | Brodnick et al. |

(Continued)

FOREIGN PATENT DOCUMENTS

| EP | 1188412 B1 | 3/2002 |
| EP | 1983895 B1 | 4/2017 |

OTHER PUBLICATIONS

Suggested Stable Chest Pain Assessment Algorithm, University of Ottawa Heart Institute, 2014, retreived from https://ottawaheart.ca. document/suggested-stable-chest-pain-assessment-algorithm, 1 page.
(Continued)

*Primary Examiner* — Deborah L Malamud
(74) *Attorney, Agent, or Firm* — Fox Rothschild LLP

(57) ABSTRACT

An electrocardiogram ("ECG") system is provided. The system includes an ECG device capable of receiving ECG signals from a lead system attached to the user. The ECG device then renders the ECG signals into ECG data, and transmits the ECG data to at least one of a user device, such as a smart phone, or a cloud-based storage system. The user device is capable of rendering the ECG data into an ECG graph, and displaying the ECG graph to the user on an application ("app"). The system also provides for a cloud-based storage system capable storing the ECG data and providing access to the ECG data to the user and to medical personal.

22 Claims, 23 Drawing Sheets

Related U.S. Application Data

(60) Provisional application No. 62/638,590, filed on Mar. 5, 2018.

(52) U.S. Cl.
CPC .......... *A61B 5/7435* (2013.01); *A61B 5/6823* (2013.01); *A61B 5/6824* (2013.01); *A61B 5/6829* (2013.01)

(58) Field of Classification Search
CPC ......... G16H 15/00; H04L 67/12; H04W 4/80; G06F 19/00; G06F 19/3418
See application file for complete search history.

(56) References Cited

U.S. PATENT DOCUMENTS

| | | | |
|---|---|---|---|
| 6,453,186 | B1 | 9/2002 | Lovejoy et al. |
| 6,690,967 | B2 | 2/2004 | Meij et al. |
| 7,733,224 | B2 | 6/2010 | Tran |
| 11,529,085 | B1 | 12/2022 | Vajdic |
| 2008/0154110 | A1 | 6/2008 | Burnes et al. |
| 2009/0171227 | A1 | 7/2009 | Dziubinski et al. |
| 2012/0160250 | A1 | 6/2012 | Lavigne |
| 2013/0231947 | A1* | 9/2013 | Shusterman ........... G16H 40/67 705/2 |
| 2014/0081118 | A1 | 3/2014 | Reinhold, Jr. et al. |
| 2014/0316813 | A1 | 10/2014 | Bauer |
| 2016/0287166 | A1* | 10/2016 | Tran ......................... A61B 5/74 |
| 2017/0164855 | A1 | 6/2017 | Solosko et al. |
| 2019/0269344 | A1 | 9/2019 | Shah |
| 2022/0022796 | A1 | 1/2022 | Cho et al. |

OTHER PUBLICATIONS

B.E. Backus et al., Risk Scores for Patients with Chest Pain: Evaluation in the Emergency Department, Current Cardiology Reviews, 2011, vol. 7, No. 1, pp. 2-8.

Charles V. Pollack and Sarah M. Perman, Chest Pain in the Emergency Department: Different Diagnosis, The Cardiology Advisor, 2013, retreived from http://www.thecardiologyadvisory.com/home/decision-support-in-medicine/cardiology/chest-pain-in-the-emergency-department-differential-diagnosis.

Ercenk Keresteci, Extracting Insights from IoT, Solution Guide, Azure Industries Experiences, Microsoft Corporation, 2018 (14 pages).

Extended European Search Report for European Application No. 19763341.5, filed Jul. 17, 2020 mailed Mar. 4, 2022.

International Patent Application No. PCT/US2019/02834, International Search Report and Written Opinion, mailed May 14, 2019.

International Search Report and Written Opinion for International Application No. PCT/US24/26901, filed Apr. 29, 2024, mailed Oct. 11, 2024.

\* cited by examiner

MOBILE ELECTROCARDIOGRAM SYSTEM

CROSS-REFERENCE TO RELATED APPLICATIONS

This application is a continuation of U.S. patent application Ser. No. 16/293,573, filed Mar. 5, 2019, which claims the benefit of U.S. Provisional Application 62/638,590 filed Mar. 5, 2018, the entire disclosure of which is expressly incorporated herein by reference.

BACKGROUND

Technical Field

The present disclosure relates generally to the field of medical devices. More specifically, the present disclosure relates to a mobile Electrocardiogram ("ECG") system and method of use.

Related Art

There are 700-750,000 heart attacks in the United States annually, of which 210,000 are recurrent events. In addition, 8-10 million patients visit the emergency room ("ER") annually for chest pain. Through the process of interviewing practicing clinicians, it is readily apparent that there are numerous recurrent visits to the ER. These result in costly hospital stays for patients who have had myocardial infarction ("MI"). There is a push by the insurance and hospital industries to reduce these visits, as well as other "unnecessary" visits to the ER. Of all the chest pain ("CP") visits to the ER, only 0.06% are true life-threatening emergencies once per prognosticator indicators have been accounted for.

The consequences of each CP visit to the ER are psychological, as well as direct and indirect economic costs. Once a patient has had an acute coronary syndrome ("ACS") event, especially at a young age (under 65 y/o), the psychological ramifications are significant. Those patients typically live in fear of their cardiac status and the fear of having another myocardial infarction ("MI"). This effect also spills over to their immediate friends, family and co-workers, some of whom may become worried about their own mortality. Post-MI depression occurs affects 1 in 6 patients and 2 out of every 6 patients have some signs/symptoms of depression leading to increased mortality rates within the first 6 months. According to various medical sources, up to 12% of the post-ACS patients develop Post-Traumatic Stress Disorder ("PTSD") which results in a doubling of their risk of another ACS event and mortality within 1-3 years.

The economic implications of chest pain are quite significant. Table 1 demonstrates the potential economic damages to the patient from an unnecessary visit to the ER:

TABLE 1

(US Government 2017, 2018 Health Plan and Prices)

| Typical Site of Visit in the US system | Average cost per use in the US System |
|---|---|
| Ambulance | $300 |
| ER Co-Pay | $0-$300 |
| Observation level stay in the hospital | $2500-$5000 |
| Loss of Wages due to ER visit or | $162 - See median income $59,039/ |

TABLE 1-continued (US Government 2017, 2018 Health Plan and Prices)

| Typical Site of Visit in the US system | Average cost per use in the US System |
|---|---|
| hospital stay | 365 days, Loudenback 2017 |
| Visit to primary care physician | $15-$30 |
| Visit to specialist | $30-$100 |

These prices are approximate depending on the patients health plan. Many patients must meet deductibles of $2500-$6000 before their insurance covers the cost of an ER visit or even an observation stay in the hospital.

Cost to Hospitals:
1. Economic loss from extended stays:
   a. Hospitals are reimbursed $800-$2000 per observation stay; therefore, any stay longer than 14 hours will likely result in an economic loss;
      i. Unnecessary in-hospital testing will result in a loss as well;
      ii. ER over-crowding results in slower treatment for patients who truly need immediate care; and
      iii. Repeat patient visits to the ER result in heavy losses.

Societal Cost (See Appendix 2, Indirect cost projections to 2035):
1. Increasing insurance premiums/deductibles;
2. Loss of productivity due to sick days;
3. Diversion of vital resources from those who need services; and
4. Contribution to rising cost of healthcare.

The goals of the US healthcare system are to reduce the cost of care, expedite care, reduce length of stay in the hospital, and reduce readmission rates while maintaining quality of care. This includes maintaining low complication rates and improving patient satisfaction In order to do so, hospitals across the US have been providing value added services at their own expense, such as telehealth services for congestive heart failure ("CHF") management. The current reimbursement model results in a very low profit margin for chest pain services. Thus, anything a hospital can do to reduce unnecessary admissions is in its best interest.

The unsettled and rapidly expanding space is the world of wearables technology provides immediate biofeedback to the wearer. By various estimates, the mHealth (mobile health) market is poised to grow into a multi-billion dollar industry. Still in its infancy, advancements in micro-technology, micro-processing, and software development allow innovators to develop products which were either only dreamed about 10-20 years ago or allow legacy devices to be miniaturized and repurposed for mobile platforms. Those individuals willing to be engaged will find a supply of products to meet many of their healthcare needs. The thrust for these devices is to liberate patients from costly tests, reduce financial burdens on the patient and healthcare system, and create an environment which motivates individuals to adhere to a prescribed regimen. Accordingly, these and other needs are addressed by the mobile ECG system of the present disclosure.

SUMMARY

This present disclosure relates to a mobile ECG system and method of use. The system includes a portable, easyto-use ECG device that allows users to record ECG data, and to transmit the ECG data to a user device. Additionally, the system provides for a cloud-based storage system capable storing the ECG data and providing access to the ECG data to the user and to medical personal.

The ECG system in accordance with the present invention includes a mobile ECG device designed to provide medical-quality tracings at a cost affordable to the average American. Unlike the traditional 12-lead ECG, the ECG device can be a 9-lead system which would capture the majority of acute coronary syndromes by coupling ECG data with interactive software which together would risk stratify the need for emergent medical care. Utilizing the ability to compare serial ECGs and being able to accurately assess changes in the ST-segment and T waves along with the input of symptoms and basic vital signs, the ECG system would capture the majority of heart attacks as well as assisting in differentiating cardiac from non-cardiac chest pain so that the user is able to make an educated decision on whether or not a visit to the ER is warranted. This is accomplished by utilizing evidence-based algorithms which have already been incorporated into current clinical practices.

The ECG system is generally designed with simplicity in mind. For the limb leads, either a 4-bracelet system, 1 for each wrist, and 1 for each ankle can be used. Also, the Mobile ECG system can be designed using a zero-bracelet, a 2-bracelet and 3-bracelet system.

The signal processing used in the ECG system can be incorporated into a chest plate housing with wireless electrocardiographic transmission to a user device, such as a smart phone, tablet or laptop. An additional iteration of the ECG system can include a separate processing unit which will be connected either wirelessly or by wire. The processing unit can be configured to transmit the electrocardiogram to the user device. In addition, due to the chest device, the ECG system can be configured to monitor and/or measure the respiratory rate of the wearer.

The ECG system is configured to utilize the electrocardiographic data and compare such data with prior electrocardiographic data and provide a comparison by analyzing such measurements from the user. In addition, the ECG system can be configured to display the respiratory rate of the user.

The ECG device, through the utilization of modern technology, redesigns and reinvents the ECG machine to provide complete portability. The ECG is a critical component of the diagnostic portfolio, currently available only in the ER/hospital setting or a physician's office.

In the short term, the ECG demonstrates irreplaceability through the accuracy of its ECG tracing and comparison capabilities and the accuracy of its risk stratification capacity through a learning interactive algorithm. Customer retention and improvement follows through continued hardware and software improvements. Service line expansion occurs by offering a cheaper device with limited capabilities but enhanced software for chronic disease state management.

Currently, no commercially available devices/systems address this issue. There are multiple manufacturers of single-lead ECG systems which monitor only basic arrhythmia and heart rate monitoring; such systems are inadequate to assist in the differentiation of cardiac from non-cardiac chest pain. Home telehealth companies currently utilize Bluetooth-connected oximeters, scales, and blood pressure cuffs for CHF patients. The information is sent to a monitoring center and requires a nurse to review the data, review the information with the patient's physician, and then guide the patient on medication changes.

BRIEF DESCRIPTION OF THE DRAWINGS

The foregoing features of the invention will be apparent from the following Detailed Description of the Invention, taken in connection with the accompanying drawings, in which.

DETAILED DESCRIPTION

The present disclosure relates to a mobile Electrocardiogram ("ECG") device and method of use, as described in detail below in connection with FIGS. 1-23.

Figure 1:
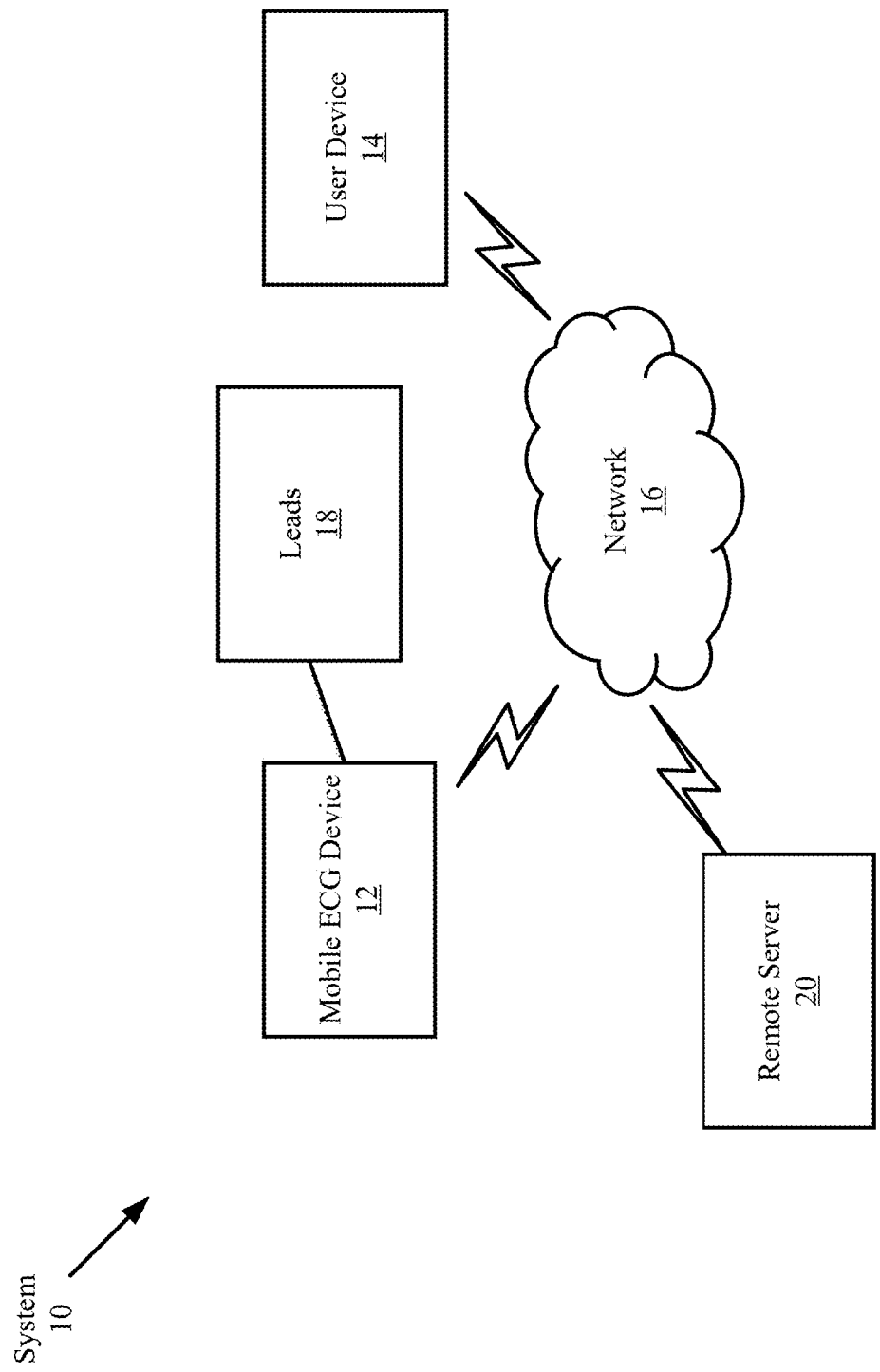
FIG. 1 is a diagram illustrating the electrocardiogram ("ECG") system of the present disclosure.

FIG. 1 is a diagram illustrating a mobile ECG system, indicated generally at 10. The system includes an ECG device 12, a user device 14, a network 16, lead(s) 18, and a remote server 20. The ECG device 12 is a mobile device capable of capturing and transmitting ECG data obtained from the one or more leads 18. The ECG data includes digital or analog signals. The lead(s) 18 is a electrical connection connected to the ECG device 12 on one end, and to an electrode on the other end. The electrode is attached to a body part or appendage and is capable of capturing the ECG signals. The user device 14 can be any electronic device such as a mobile phone, a tablet computer, a smartphone, a phablet, an embedded device, a personal computer, a desktop computer, a wearable device, a field-programmable gate array ("FPGA"), an application-specific integrated circuit ("ASIC"), etc. The ECG device 12, the user device 14, and the leads 18 will be discussed in further detail below.

The network 16 can be any type of wired or wireless network, including but not limited to, a legacy radio access network ("RAN"), a Long Term Evolution radio access network ("LTE-RAN"), a wireless local area network ("WLAN"), such as a WiFi network, an Ethernet connection, or any other type network. The ECG device 12 can be connected to the user device 14 via a wireless network connection (e.g., Bluetooth, WiFi, LTE-RAN, etc.) or a direct wired connection between the ECG device 12 and the user device 14 (e.g., a wired universal serial bus (USB)) connection. Optionally, mobile ECG device 12 and the user device 14 could communicate with a remote server 20. The remote server 20 can be any type of server used for data storage, such as, for example, a hard drive, a cloud storage repository (e.g., Dropbox, Google Drive, etc.), etc. The remote server 20 can receive data via the network 16 from the ECG device 12 and the user device 14.

Figure 2:
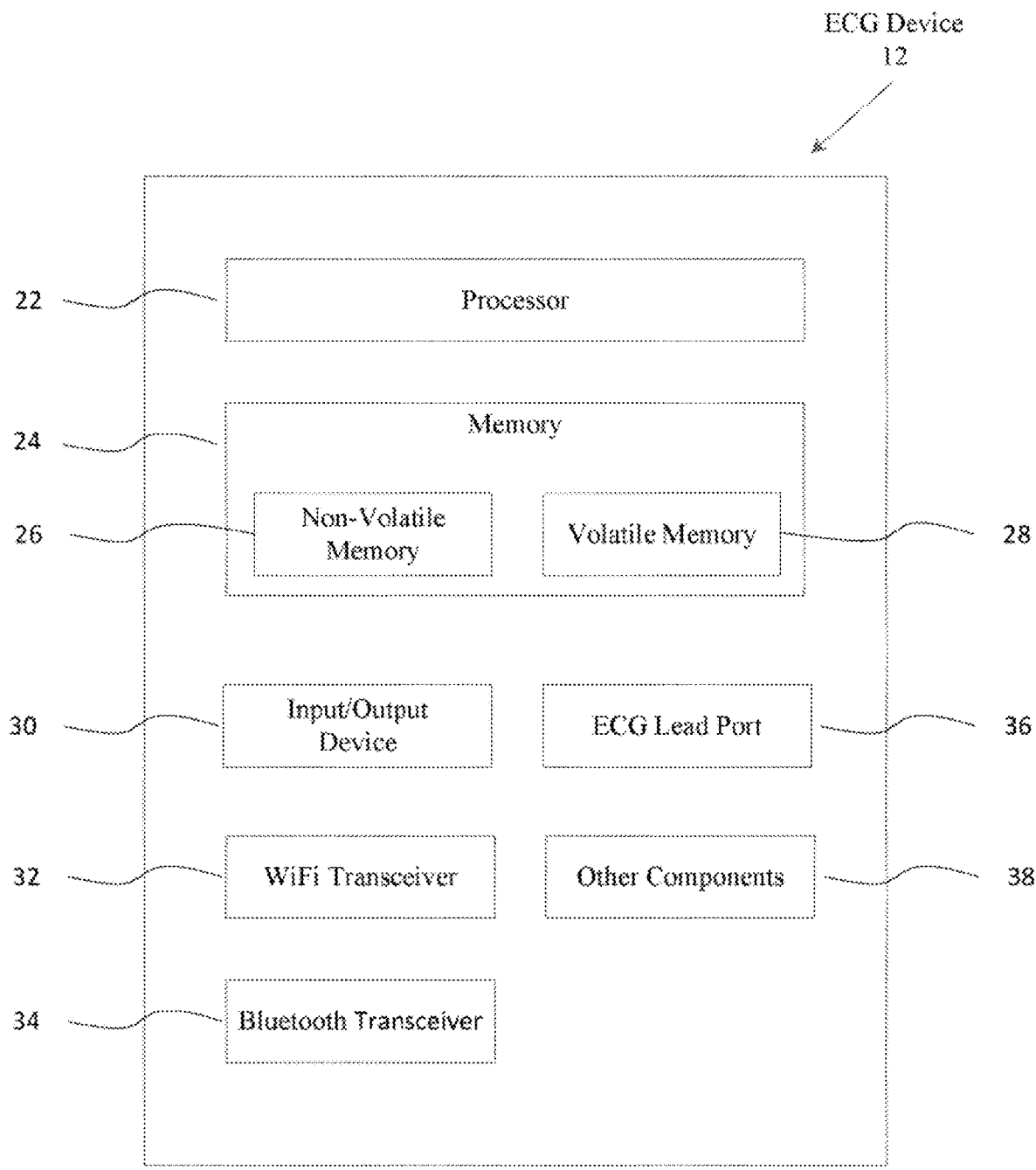
FIG. 2 is a diagram illustrating the hardware and software components of an ECG device of the present disclosure.

FIG. 2 is a diagram illustrating components of the ECG device 12 in greater detail. The ECG device 12 includes a processor 22, a memory 24, an input/output device 30, a WiFi transceiver 32, a Bluetooth transceiver 34, an ECG lead port 36, and other components 38. The processor 22 executes software/firmware modules for controlling the ECG device 12, such as a WiFi connection module, a Bluetooth connection module, software/firmware for detecting electrical activity of the heart (as described in greater detail below), etc. The memory 24 can be a hardware component configured to store data related to operations performed by the ECG device 12. Specifically, the memory 24 can store ECG data received from the leads 18. The memory can include any suitable, computer-readable storage medium such as a disk, non-volatile memory 26 (e.g., read-only memory ("ROM"), erasable programable ROM ("EPROM"), electrically-erasable programmable ROM ("EEPROM"), flash memory, etc.), volatile memory 28, (e.g., random access memory ("RAM"), dynamic random-access memory ("DRAM"), etc.) or other types of storage media. The input/output device 30 is a hardware component that enables a user to enter inputs and display results, such as a display, touchscreen, etc.

The WiFi transceiver 32 could include any suitable, commercially-available transceiver configured to transmit and/or receive data via a WiFi frequency band, and which enables communication with other electronic devices directly or indirectly through a WiFi network based upon the operating frequency of the WiFi network. The Bluetooth transceiver 34 could include any suitable, commercially-available transceiver configured to transmit and/or receive data via a Bluetooth connection, and which enables communication with other electronic devices directly or indirectly through a Bluetooth connection based upon the operating frequency of the Bluetooth wireless technology standard. It be understood that the ECG device 12 can include either or both of the transceivers (WiFi transceiver 32 and Bluetooth transceiver 34), or any other suitable transceivers, such as, but not limited to, Zigbee transceivers, LTE transceivers, 3G legacy transceivers, etc.

The ECG lead port 36 could include any suitable port for connecting an ECG lead system to the ECG device 12. The ECG lead system includes one or more leads 18 connected to an electrical connection clip on one end (e.g., an octopus cable), and a mean to connect to one or more electrodes on the other end (e.g., an alligator clip). The electrical connection clip can be inserted into the ECG lead port 36. Each electrode can be placed on a patient's limbs (e.g., arms and legs), or chest. The ECG lead system can comprise any number of leads 18 producing any number of channels output. For example, the ECG lead system can include 10 leads producing a 12 channel output, 7 leads producing a 9 channel output, which is expandable to a 12 channel output (e.g., 6 limb lead output: aVR, aVL, aVF, I, II, III; chest leads: V2, V3, V4 expandable to V1, V2, V3, V4, V5, V6), etc.

For limb leads, a bracelet system can be used, such as, for example, 4-bracelet system, a zero-bracelet, 2-bracelet, and 3-bracelet system. The 4-bracelet system can include one lead for each wrist and one lead for each ankle. The zero-bracelet system can be in the form of a fully wearable chest piece with all of the necessary leads incorporated into a chest and abdomen plate. In this arrangement, 3-5 precordial leads can be used in addition to an extension towards both shoulders and both hips so as to complete the zero bracelet system. The 2-bracelet system can include a bracelet for each ankle and the chest piece can house 3-5 precordial leads and have two extensions, one towards each shoulder for the remaining limb leads. The 3-bracelet system can include a chest piece with 3-5 precordial leads and an extension lead towards either the right or left shoulder along with one bracelet for either the right or left wrist and one bracelet for each ankle. The chest piece can include chest patches which include adjustable components for body sizing and location placement.

Alternatively, the electrodes can each comprise wireless functionality where each electrode transmits ECG data wirelessly to the ECG device 12 or the user device 14. For example, each electrode, bracelet and chest piece can comprise a processor and/or a wireless transceiver (e.g., Bluetooth transceiver, WiFi transceiver, etc.) or transmitter to transmit the ECG data to a transceiver in the ECG device 12 or in the user device 14.

The other components 38 can be a battery, wireless charging device, a power port/cable, an audio output device, an audio input device, a data acquisition device, a USB port, one or more further ports to electronically connect to other electronic devices, a respirometer body temperature sensor, an oxygen sensor, a blood pressure sensor, a global positioning system ("GPS") device, a movement/motion accelerometer, a body weight/fat sensor, etc.

By way of example, the ECG device 12 can include a chest patch with a wire extension toward a left shoulder and from the left shoulder to a right shoulder, another wire extension from a chest patch towards a left hip and from the left hip towards a right hip. The ECG device 12 can connect to the chest patch. By way of another example, the ECG device 12 can be incorporated into a wearable clothing item or other sleeve/accessory design with integrated sensors and transmitters with adjustments for different body sizing.

Figure 3:
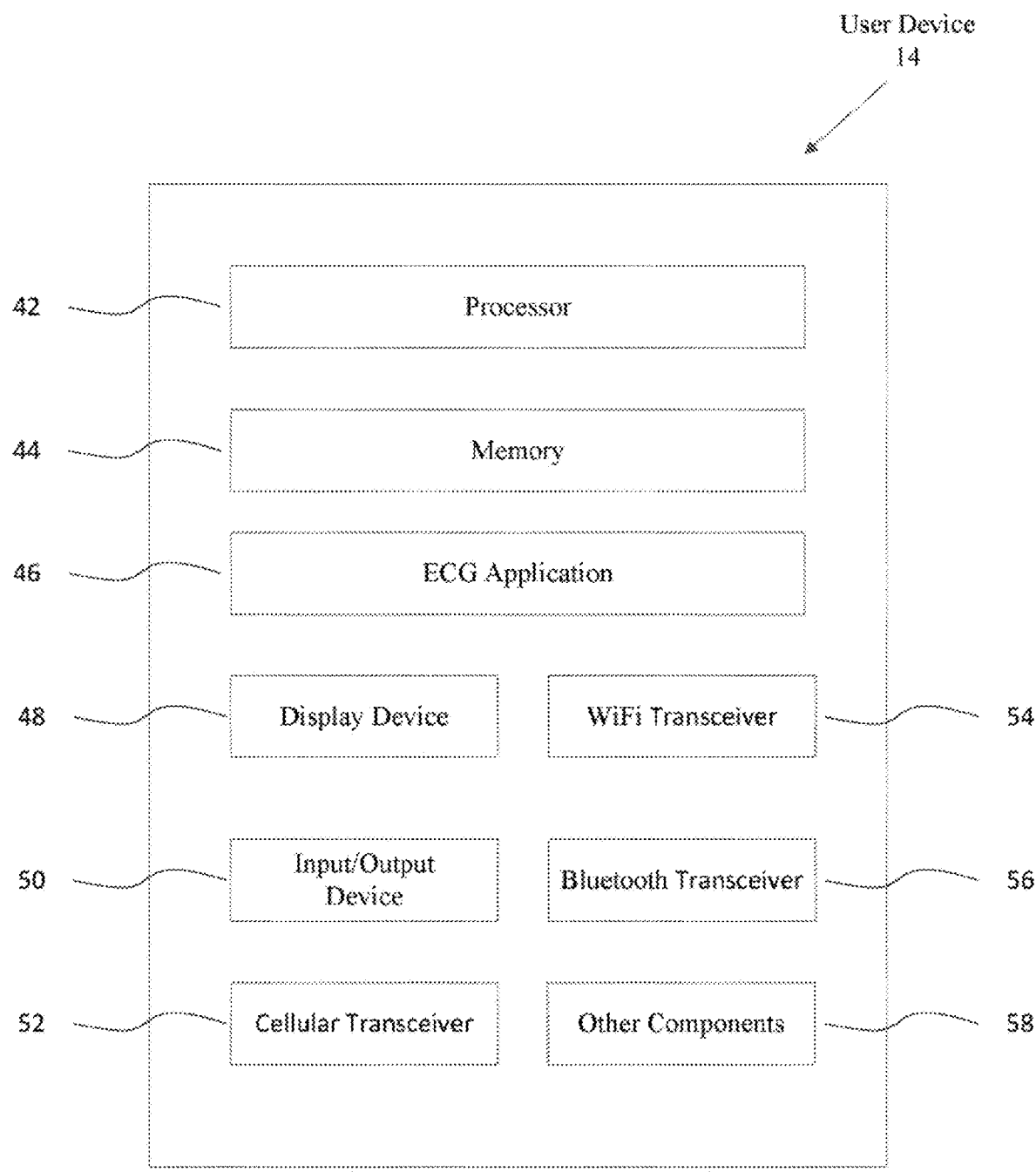
FIG. 3 is a diagram illustrating the hardware and software components of a user device (e.g., a smart phone) in communication with the recorder.

FIG. 3 is a diagram illustrating the user device 14 in greater detail. As discussed above, the user device can be a portable device such as a smartphone, a laptop, a tablet, etc., or a stationary device such as a desktop terminal. The user device 14 includes a processor 42, a memory 44, an ECG application 46 which is stored in the memory 44 and executed by the processor 42, a display device 48, an input/output device 50, a cellular transceiver 52, a WiFi transceiver 54, a Bluetooth transceiver 56, and other components 58. The processor 42 can be configured to execute one or more applications of the user device 14. For example, the applications can include a web browser, the ECG application 46, etc. The memory 44 can be a hardware component configured to store data related to operations performed by the ECG device 12. For example, the memory 44 can store data received from the ECG device 12. The memory can include any suitable, computer-readable storage medium such as a disk, non-volatile memory (e.g., read-only memory ("ROM"), erasable programmable ROM ("EPROM"), electrically-erasable programmable ROM ("EEPROM"), flash memory, etc.), volatile memory, (e.g., random access memory ("RAM"), dynamic random-access memory ("DRAM"), etc.) or other types of storage media.

The ECG application 46 is a software application ("app") that can communicate with the user device 14 via, for example, a Bluetooth or a WiFi wireless connection. The ECG application 46 can also perform other functions, such as initiate a connection pairing, receive user inputs, transmit the user inputs to the ECG device 12, receive data from the ECG device 12, manage the data, change parameters of the ECG device 12 or the ECG application 46, show an electrocardiogram received from the ECG device 12, receive ECG data from a third party, etc. Additionally, the ECG application can store data collections, surveys, psychological states, recommended diets/exercises, patient diets/exercises, medications, medical histories, symptoms, activities, lifestyles, recommend proper leads/sensor placements, etc. These functions will be explained in greater detail below. The ECG application 46 can have security features for ensuring HIPPA compliance, including data encryption and user identity.

The display device 48 can be a hardware component configured to show data to a user. The input/output device 50 can be a hardware component that enables the user to enter inputs. The display device 48 and the input/output device can be separate components or integrated together, such as a touchscreen.

The cellular transceiver 52 is a hardware component configured to transmit and/or receive data via a cellular connection. Specifically, the cellular transceiver 52 enables communication with other electronic devices directly or indirectly through a cellular network (e.g., an LTE network, a legacy network, etc.) based upon the operating frequency of the cellular network.

The WiFi transceiver 54 could include any suitable, commercially-available transceiver configured to transmit and/or receive data via a WiFi frequency band, and which enables communication with other electronic devices directly or indirectly through a WiFi network based upon the operating frequency of the WiFi network. The Bluetooth transceiver 56 could include any suitable, commercially-available transceiver configured to transmit and/or receive data via a Bluetooth connection, and which enables communication with other electronic devices directly or indirectly through a Bluetooth connection based upon the operating frequency of the Bluetooth wireless technology standard.

The other components 58 can include a battery, an audio output device, an audio input device, a data acquisition device, one or more ports to electronically connect to other electronic devices, etc. The process steps of the invention disclosed herein could be embodied as computer-readable software/firmware code executed by the user device 14, and could be programmed using any suitable programming languages including, but not limited to, C, C++, C #, Java, Python or any other suitable language without departing from the spirit or scope of the present disclosure.

Figure 4:
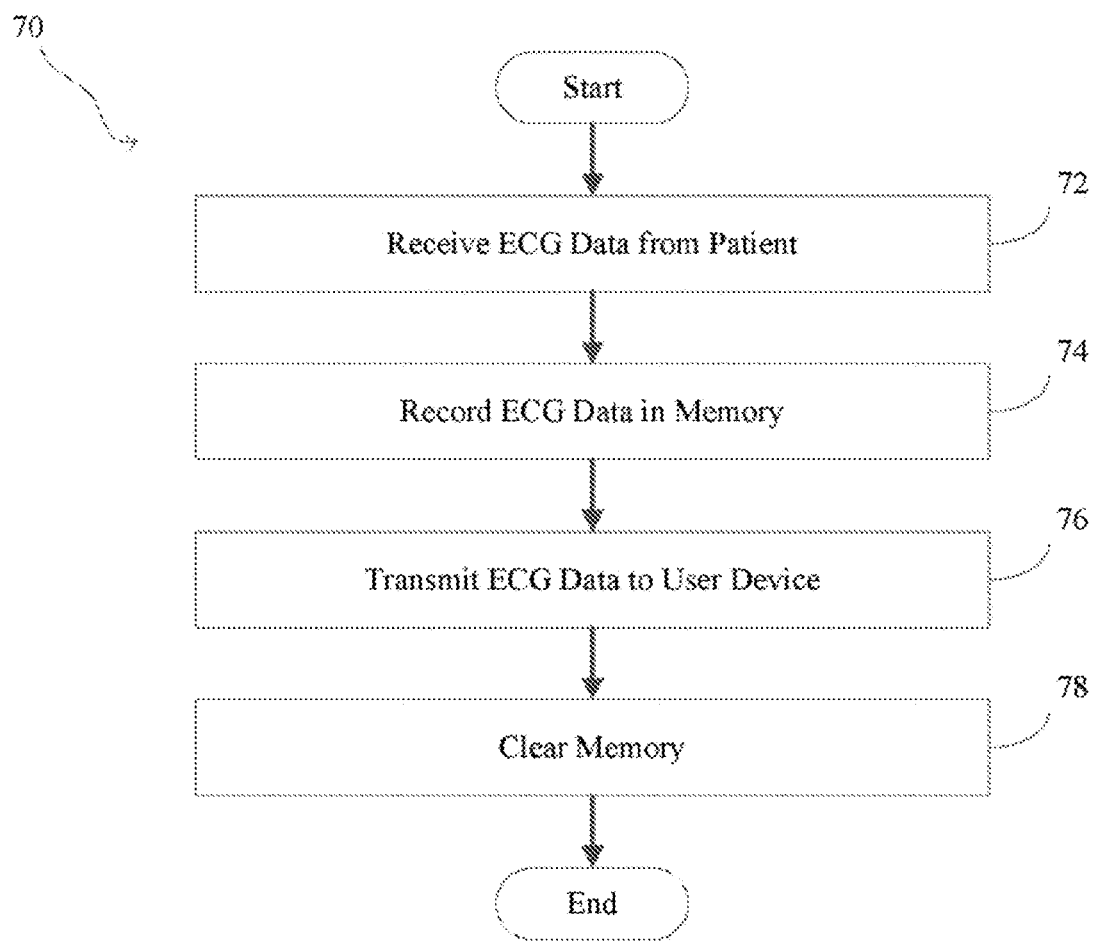
FIG. 4 is a flowchart illustrating process steps carried out by the ECG device of the present disclosure.

FIG. 4 is a flowchart illustrating process steps carried out by the ECG device 12 of the present disclosure, indicated generally at 70. In step 72, the ECG system 12 receives ECG data from a user (e.g., a patient). As discussed above, the ECG system 12 can be connected to the user via the ECG lead system. In step 74, the ECG system 12 records the ECG data onto the memory 24. The ECG data can be stored as raw data, rendered into any suitable format that can be used for storage, transmission, compression, identification, viewing, or other purposes. In step 76, the ECG device 12 transmits the ECG data to the user device 14. For example, if the user device 14 is paired to the ECG device 12 via a Bluetooth connection or a WiFi connection, the ECG device 12 can transmit the stored data to the user device 14 on the appropriate channel or band as outlined by the protocols of the wireless connection. It should be noted that the user device 14 can also render the ECG data into any suitable format.

If the ECG device 12 is not connected to or paired with the user device 14, the ECG device 12 can store the ECG data until a connection or a pairing is performed with the user device 14. In another example, the ECG device 12 can transmit the ECG data to the remote server 20. In step 78, after the ECG data has been transmitted to the user device 14 or the remote server 20, the ECG device 12 can delete the ECG data from the memory 24. Alternatively, the ECG device 12 can maintain the ECG data in the non-volatile memory 26 until a user input or predetermined condition occurs. The predetermined condition can include reaching a storage capacity threshold value, exceeding a time duration, etc.

Figure 5:
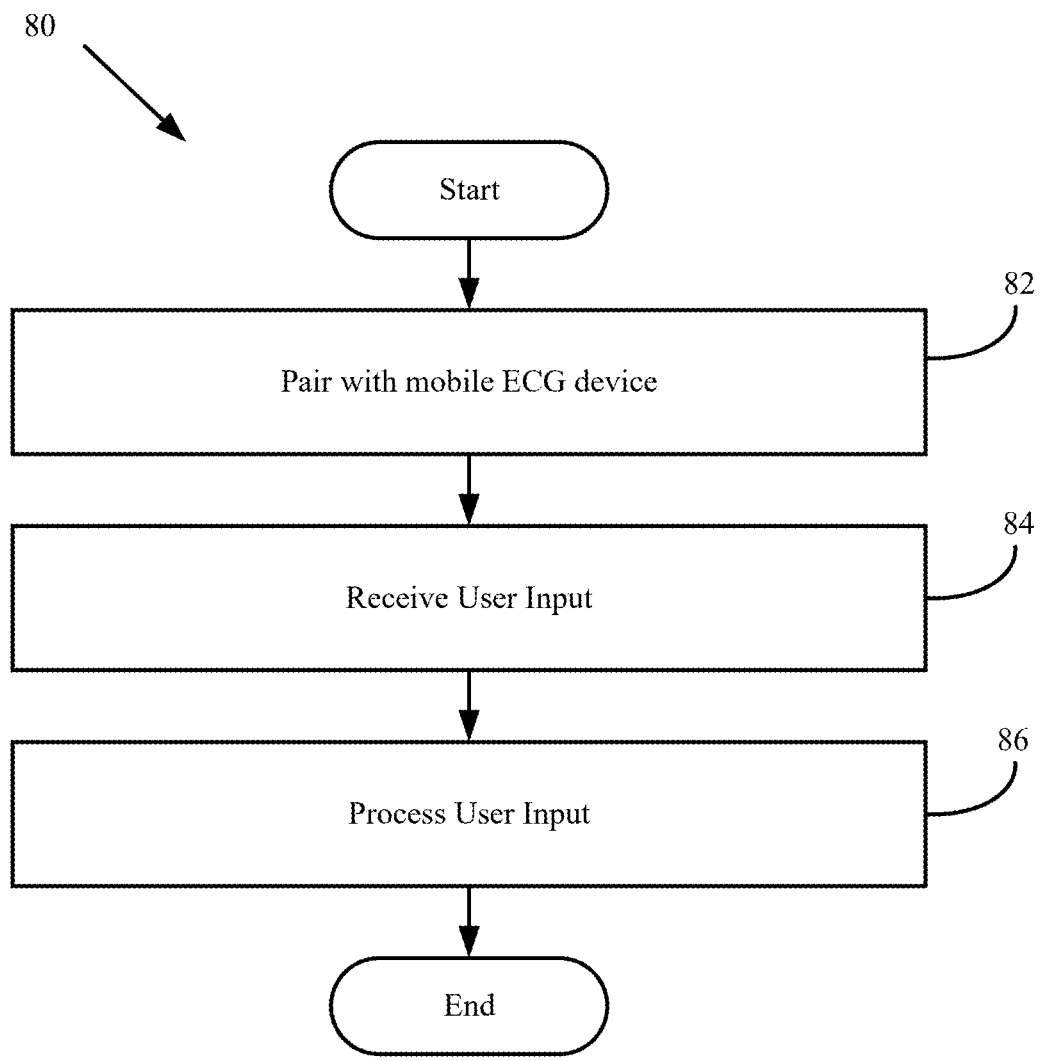
FIG. 5 is a flowchart illustrating process steps carried out by the user device of the present disclosure.

FIG. 5 is a flowchart illustrating additional process steps carried out by the user device 14 of the present disclosure, indicated generally at 80. In step 82, the user device 14 pairs with the ECG device 12. As discussed above, the user device 14 can pair with the ECG device 12 via a via a wired or other wireless connection (e.g., Bluetooth or a WiFi connection). In step 84, the user device 14 receives a user input. In a first example, the user input is a request for the ECG data from the ECG device 12. In a second example, the user input is a change in one or more parameters/settings relating to the mobile ECG device 12 or the ECG application 46. The parameters/settings can relate to data collection processes, a registration process, profile information, display options, security options (e.g., passwords, PINs, etc.) a questionnaire, WiFi network options/identifications/passwords, an IP address, remote server options (e.g., storage destination, account settings, etc.), memory storage size (e.g., a maximum size for storing on the non-volatile memory 26, volatile memory 28, and/or the memory 44), etc. Other examples of the parameters/settings can include options such as allowing the ECG device 12 to use a cellular network of the user device 14 to upload the ECG data to the remote server 20, changing setting related to the Bluetooth connection or the WiFi connection, transferring the ECG data to a further device, etc. In step 86, the user device 14 processes the user input. For example, if the user input includes the user requesting ECG date from the ECG device 12, the user device 14 can transmit a signal instructing the ECG device 12 to transmit any stored ECG data to the user device 14.

Figure 6:
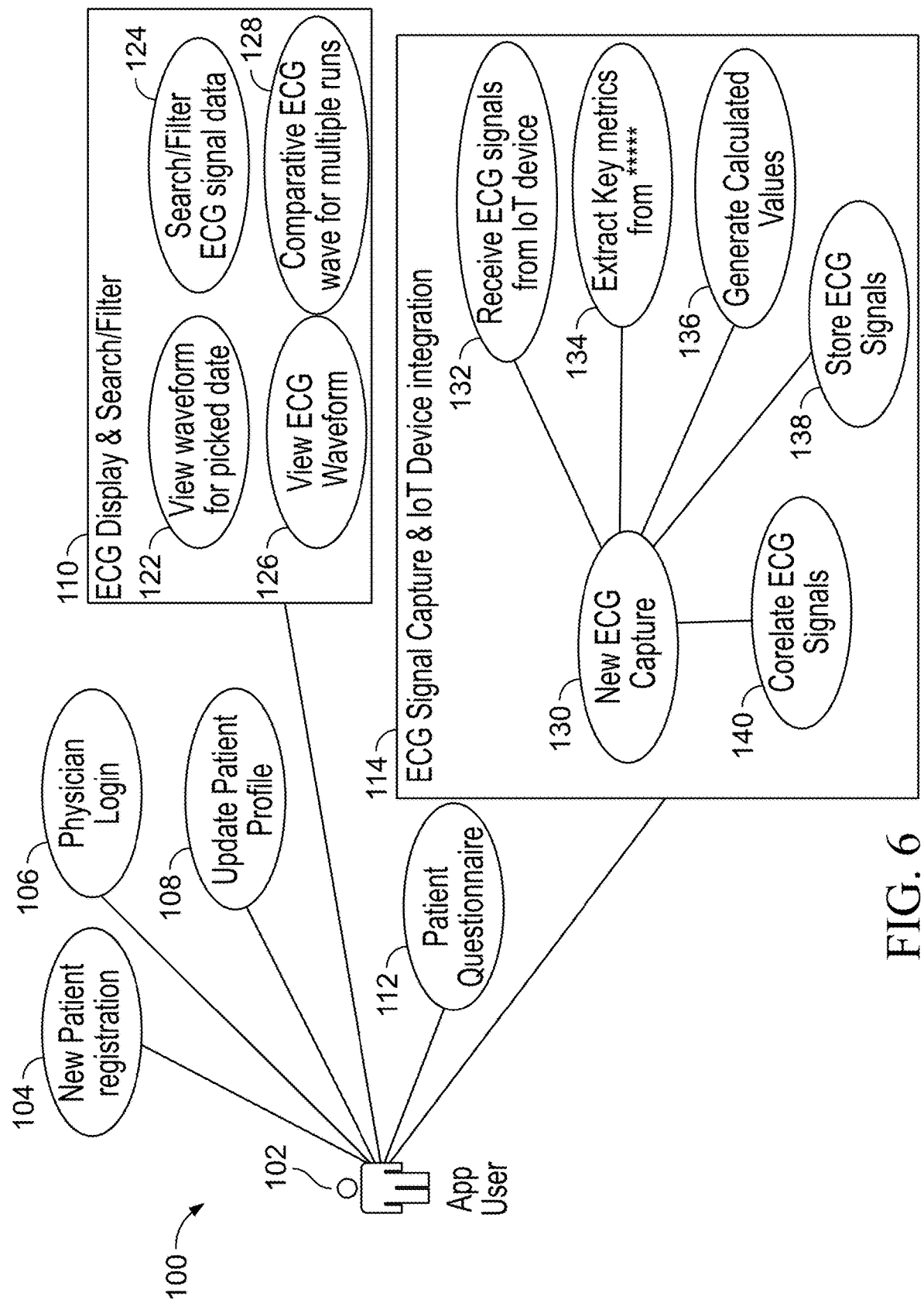
FIG. 6 is a diagram showing user functions of an ECG application of the present disclosure.

FIG. 6 is a diagram showing various user functions of the ECG application 46, indicated generally at 100. A user 102 can be a general user or a healthcare provider (e.g., a physician), each of which will have different application functionalities available. The general user can interact with the ECG application 46, and perform actions such as capture ECG signals, register, create/update a profile, submit a questionnaire, etc. These functions will be explained in greater detail below. The general user may or may not be a patient. The healthcare provider can be a doctor or a physician who is mapped to one or more general users. The healthcare provider can perform actions such as reviewing mapped general users historical data, responding to a general user's questionnaire, reviewing ECG data, and performing actions similar to those available to the general user.

In function 104, the user 102 can perform a new user/patient/physician registration. In an example, the registration process can require an email account, a social security number, a national provider identification ("NPI") number, a physician identification number ("UPIN"), etc. In function 106, the user 102 can perform a physician login. For example, the physician login can require a user name/password, a UPIN, etc. In function 108, the user 102 can update a patient profile. For example, the user 102 can update general profile information (address, height/weight, etc.) a user health history, general health details, etc.

In function 110, the ECG application 46 displays ECG data and provides searching and filtering capabilities. Specifically, in function 122, the user 102 can view previous ECG data from a selected date/time. In function 124, the user 102 can search/filter ECG signal data. In function 126, the user 102 can view (display) a current ECG waveform. In function 128, the user 102 can compare ECG data/waveforms from different readings.

In function 112, the user 102 can complete a patient questionnaire. In function 114, the user 102 can perform ECG signal capture function and internet-of-thing ("IoT") device integration. Specifically, the user 102 can connect the ECG application 46 with the ECG device 12 (via, for example, a Bluetooth connection) and receive data from the ECG device 12. More specifically, in function 130, the user 102 can perform a new ECG data capture, comprising, receiving ECG signals/data from the ECG device (function 132), extracting key metrics from the signals/data (function 134), generating calculated values (function 136), storing the ECG signals/data (function 138), and correlating the ECG signals/data (function 140). Additionally, the ECG application 46 can further allow physicians to locate patients, view ECG data authorized by the patients, and provide comments on the patients' ECG data.

Figure 7:
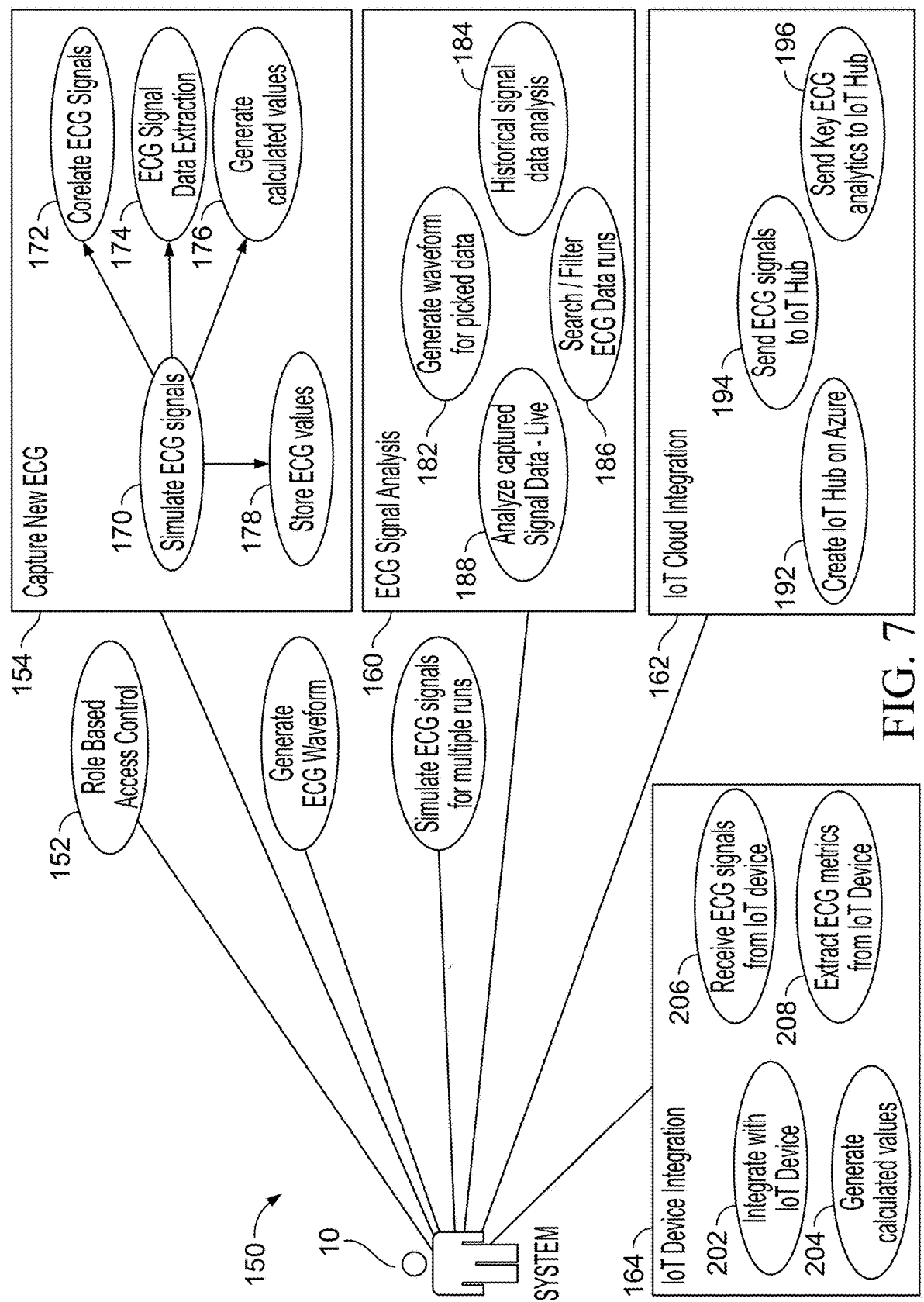
FIG. 7 is a diagram showing system functions of the ECG system of the present disclosure.

FIG. 7 is a diagram showing system functions of the system 10, indicated generally at 150. Specifically, the system 10 can provide a role-based access control function 152, a capture ECG signals/data function 154, a generate ECG waveforms function 156, a simulate ECG signals for multiple runs function 158, an ECG signal analysis function 160, an IoT cloud integration function 162, and an IoT device (e.g., the ECG device 14) integration function 164.

The capture ECG signals/data function 154 includes a simulate ECG signals function 170, a correlate ECG signals function 172, an ECG signal data extraction function 174, a generate calculated values function 176, and a store ECG values function 178.

The ECG signal analysis function 160 includes a generated waveform for a selected date function 182, a historical signal data analysis function 184, a search and filter ECG data runs function 186, and an analyze captured signal data (live) function 188. The IoT cloud integration function 162 includes a create IoT hub on a cloud computing platform (e.g., Microsoft Azure) function 192, a send ECG signals to IoT hub function 194, and a send key ECG analytics to IoT hub function 196. The IoT device integration function 164 includes an integrate with IoT device function 202, a generate calculated values function 204, a receive ECG signals from IoT device function 206, and an extract ECG metrics from IoT device function 208.

Figure 8C:
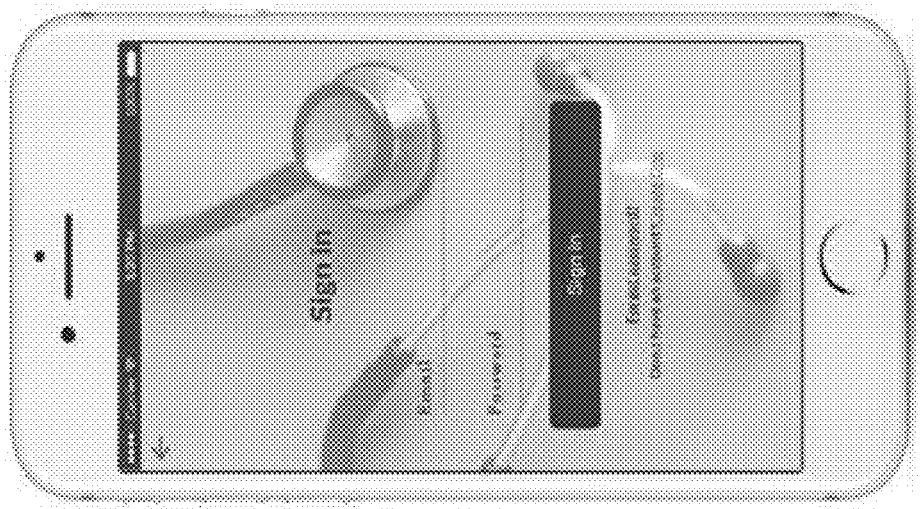
FIGS. 8A-8C are photos illustrating user interface screens generated by the user device including a home screen, a create account screen, and a sign in screen.
Figure 8B:
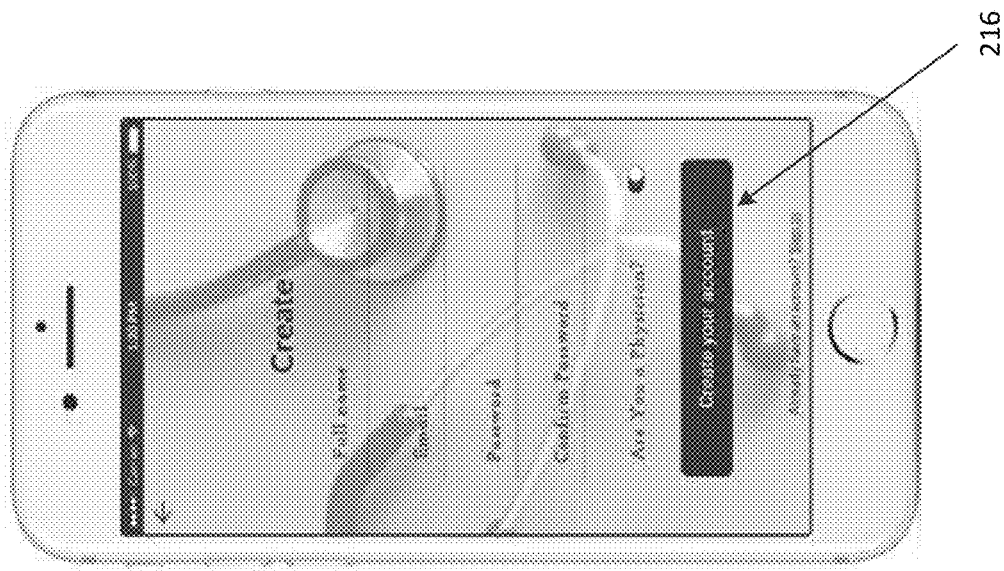
Figure 8A:
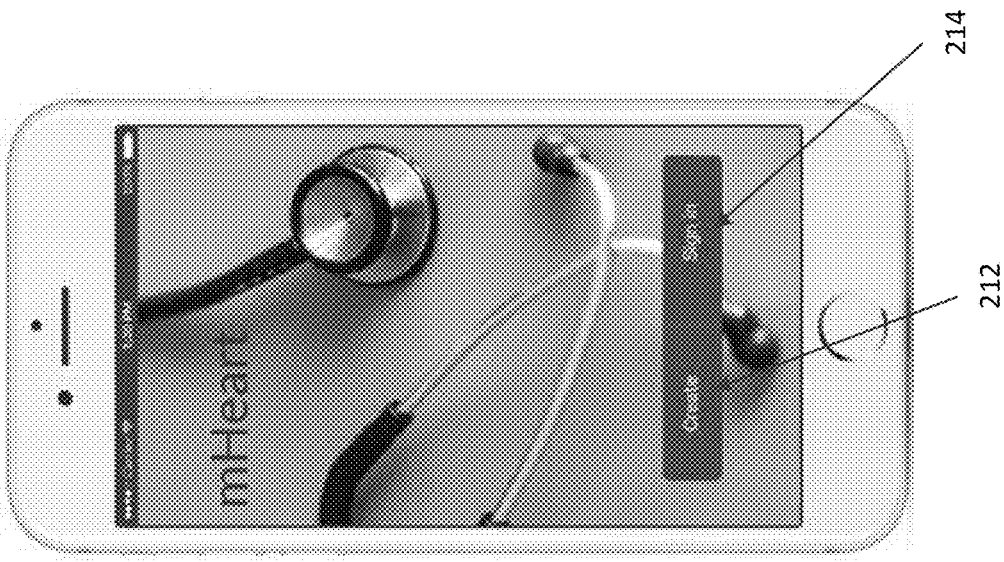

FIGS. 8A-8C illustrate user interface screens of the ECG application 46, according to the present disclosure. Specifically, FIG. 8A shows the user prompted with a create/sign in screen. In a first example, the user can select a "Create" button 212 to generate a new user/patient/physician registration using function 104. In another example, the user can select the "Sign in" button 214 to sign into the patient or physician account. FIG. 8B shows the user prompted with a create screen used to create an account. The user will enter their full name, an email address, a password, select whether they're a physician, and then select the "Create your account" button 216. If the user is a physician, the user may further be prompted to enter verification data, such as an NPI number. FIG. 8C shows a sign in screen used by a user to sign into their account. Once the user is logged into the ECG application 46, the functions of the ECG application 46 will be accessible to the user. In an example, the physician can update his/her profile, search for a patient, view a patient's ECG sessions, update or comment on a patient's ECG session, etc. In another example, the user/patient can update their profile, fill out a health questionnaire, start an ECG session, view past ECG sessions, share data with a physician, etc.

Figures 9, 10:
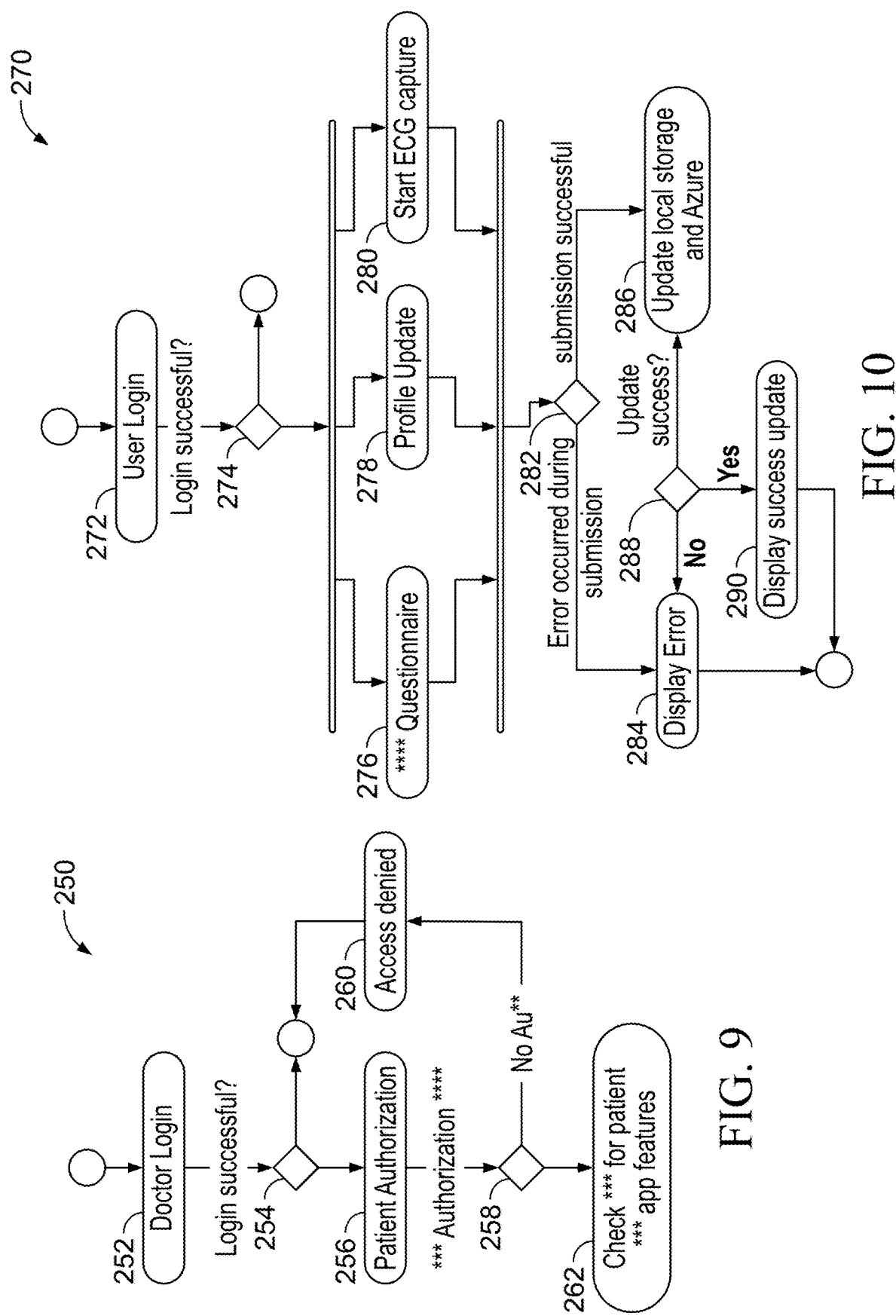
FIG. 9 is a flowchart illustrating process steps carried out by the user device of the present disclosure for a physician login process.
FIG. 10 is a flowchart illustrating process steps carried out by the user device of the present disclosure for a user login process.

FIG. 9 is a flowchart illustrating process steps for a physician login process carried out by the ECG application 46 of the present disclosure, indicated generally at 250. In step 252, the physician attempts to log into the ECG application 46 by entering required information (e.g., user name, password, etc.). In step 254, the system determines whether the login attempt is successful. If successful, in step 256, the physician requests patient authorization or requests to see patient records (e.g., ECG data). In step 258, the system determines whether the physician has authorization to view the patient records. If the physician is not authorized, in step 260, the system will prompt the physician with an access denied message. If the physician is authorized, in step 262, the system will determine which patient related features the physician is authorized to access. In an example, the patient related features include viewing a patient's ECG data, find a patient by name or other identifying information, display a list of patients with their ECG data, display ECG data with a waveform, provide comments on the ECG data, review patient questionnaires, etc.

FIG. 10 is a flowchart illustrating process steps for a user login process carried out by the ECG application 46 of the present disclosure, indicated generally at 270. In step 272, the user attempts to log into the ECG application 46 by entering required information (e.g., user name, password, etc.). In step 274, the system determines whether the login attempt is successful. If successful, in step 276, the user is presented prompted with buttons representing various functions, such as, a health questionnaire button 276, a profile update button 278, and a start ECG capture button 280. It should be understood that other functions and buttons, including any discussed within the present disclosure, can also be prompted to the user. When the user selects one of the buttons, the system, in step 282, determines whether the function of the selected button can be submitted (e.g., execute). If an error occurs during submission, in step 284, the user device 14 displays an error message. If the submission is successful, in step 286, the system updates the local storage (e.g., memory 24) and/or a cloud computing platform (e.g., Azure). In step 288, the system determines whether the update was successful. If the update is successful, in step 290, the user device 14 displays an update successful message. If the update is unsuccessful, in step 292, the user device 14 displays an update unsuccessful or error message.

Figure 11:
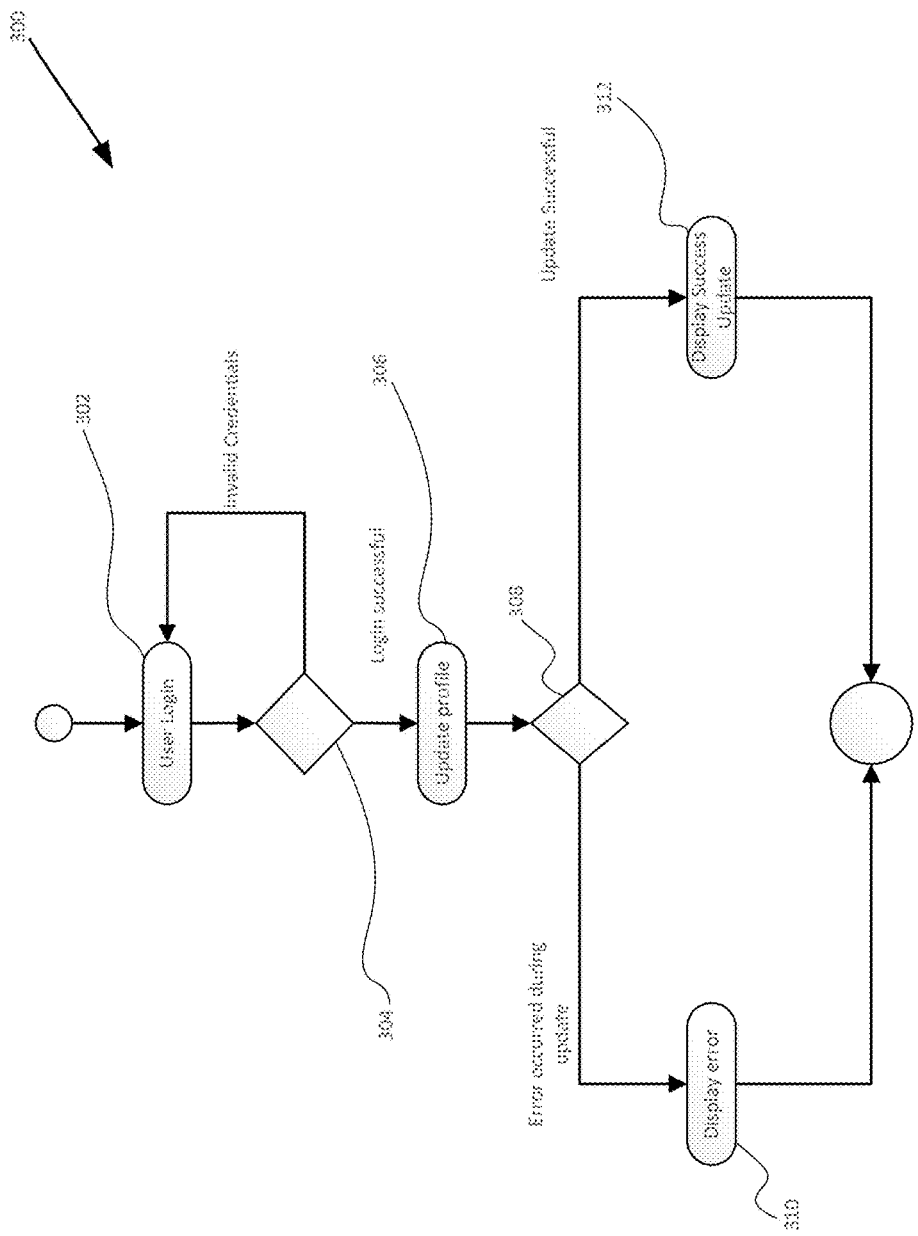
FIG. 11 is a flowchart illustrating process steps carried out by the user device of the present disclosure for a user profile update process.

FIG. 11 is a flowchart illustrating process steps for a user profile update process carried out by the ECG application 46 of the present disclosure, indicated generally at 300. In step 302, the user attempts to log into the ECG application 46 by entering required information (e.g., user name, password, etc.). In step 304, the system 10 determines whether the required information (credentials) are valid. If the credentials are invalid, the system 10 returns to step 302. If the credentials are valid, the system 10 proceeds to step 306, where the user device 14 displays to the user one or more buttons, including the update profile button. In step 306, the user selects the update profile button by, for example touching the button on a touchpad of a smartphone, and update information in the profile. The information can include, for example, personal details, contact details, a medical history, etc. Further, the user can add a physician, which would allow the physician to view the user's records, history, ECG data, etc. In step 308, the user confirms the changes by selecting an update button. If the update is successfully, in step 310, the user device 14 displays a successful update message. If the update is unsuccessfully, in step 312, the user device 14, displays an unsuccessful update or message.

Figure 12A:
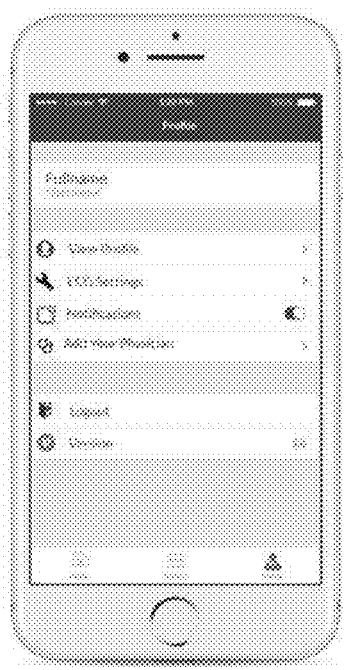
FIGS. 12A-12E are photos illustrating user interface screens generated by the user device including various profile screens as discussed in relation to FIG. 11.
Figure 12B:
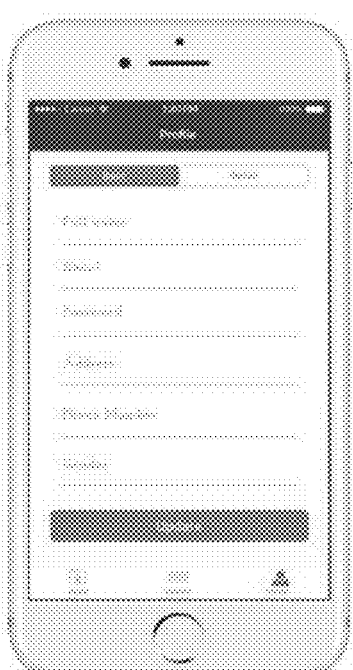
Figure 12C:
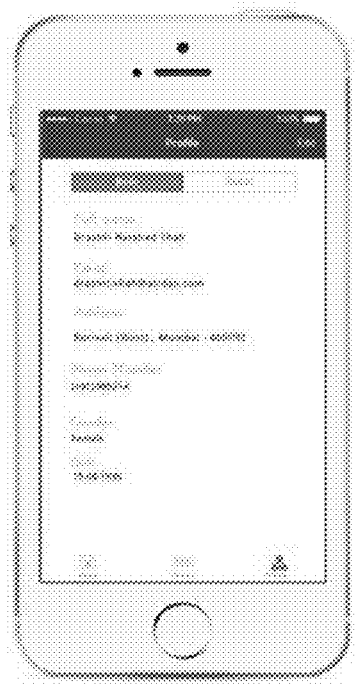
Figure 12D:
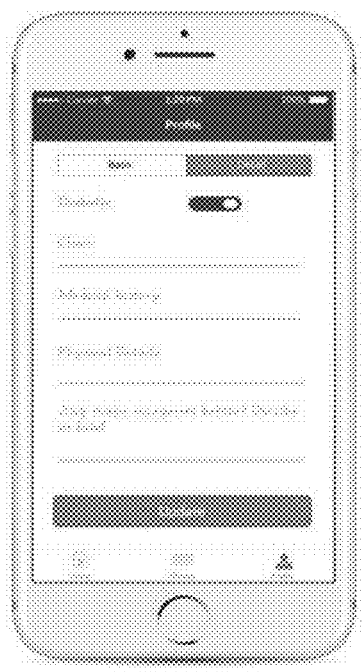
Figure 12E:
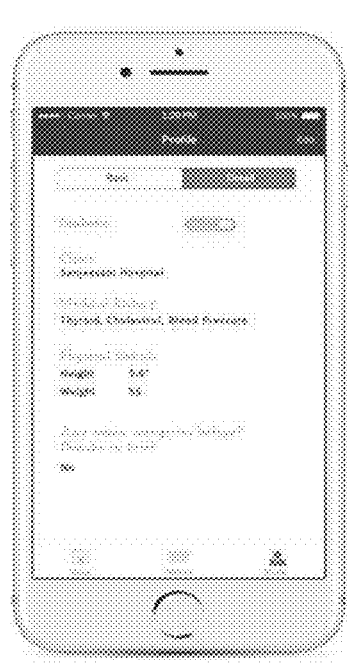

FIGS. 12A-12E illustrate example user interface screens of the ECG application 46, according to the present disclosure. Specifically, FIGS. 12A-12E show various profile screens as discussed above in relation to FIG. 11. More specifically, FIG. 12A shows a profile interface where the user can select functions, such as view profile, ECG settings, notifications (turn on/off), add a physician, logout, and view version data. FIG. 12B shows the profile interface where the user can enter basic information, such as a name, email address, password, home address, phone number, and gender. FIG. 12C shows the profile interface where the user can view his/her previously entered basic information. FIG. 12D shows the profile interface where the user can enter detail information, such as whether the user is a diabetic, a clinic name, a medical history, physical details, and whether the user had any major surgeries. FIG. 12E shows the profile interface where the user can view his/her previously entered detail information.

Figure 13:
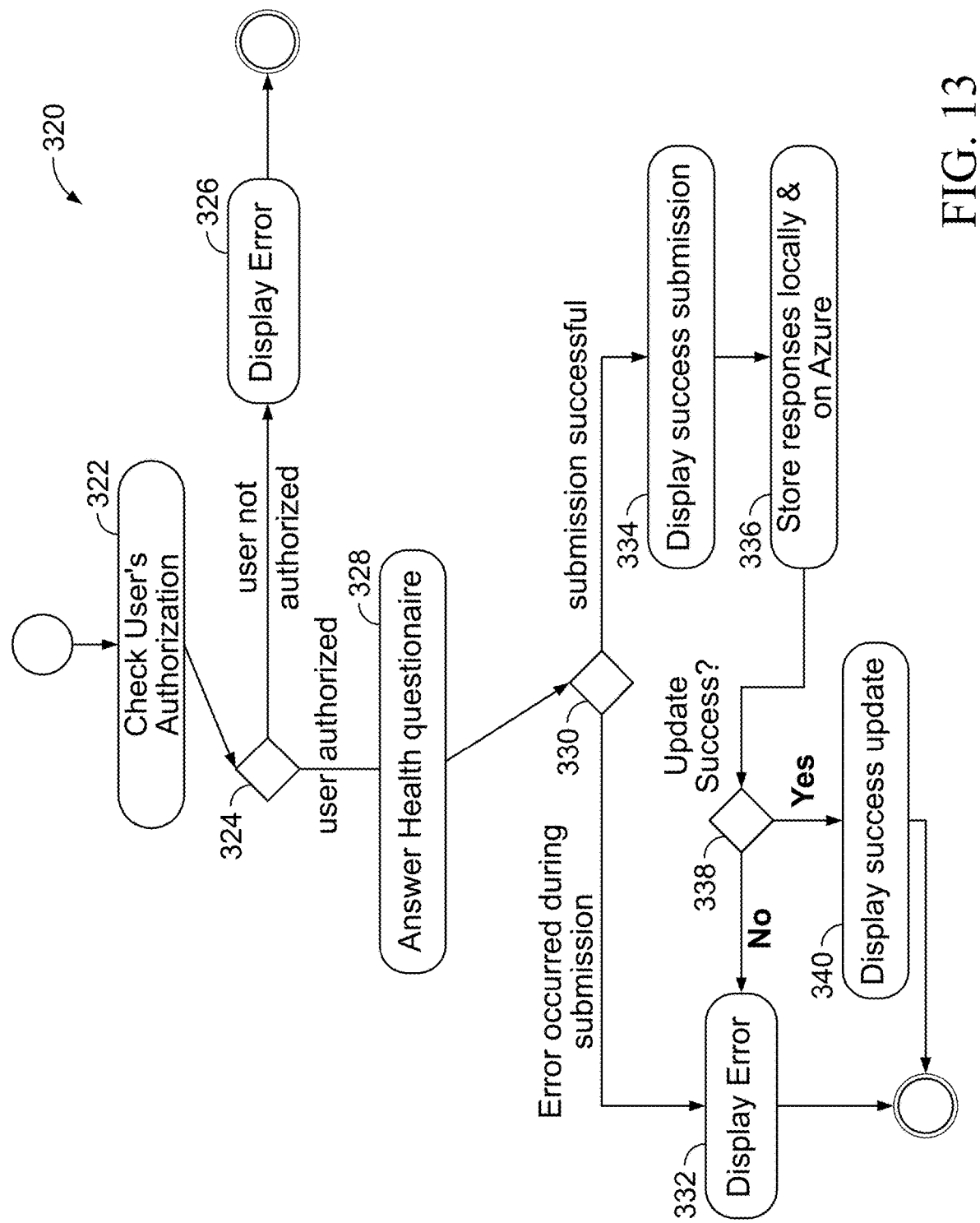
FIG. 13 is a flowchart illustrating process steps carried out by the user device of the present disclosure for answering a health questionnaire.
Figure 14A:
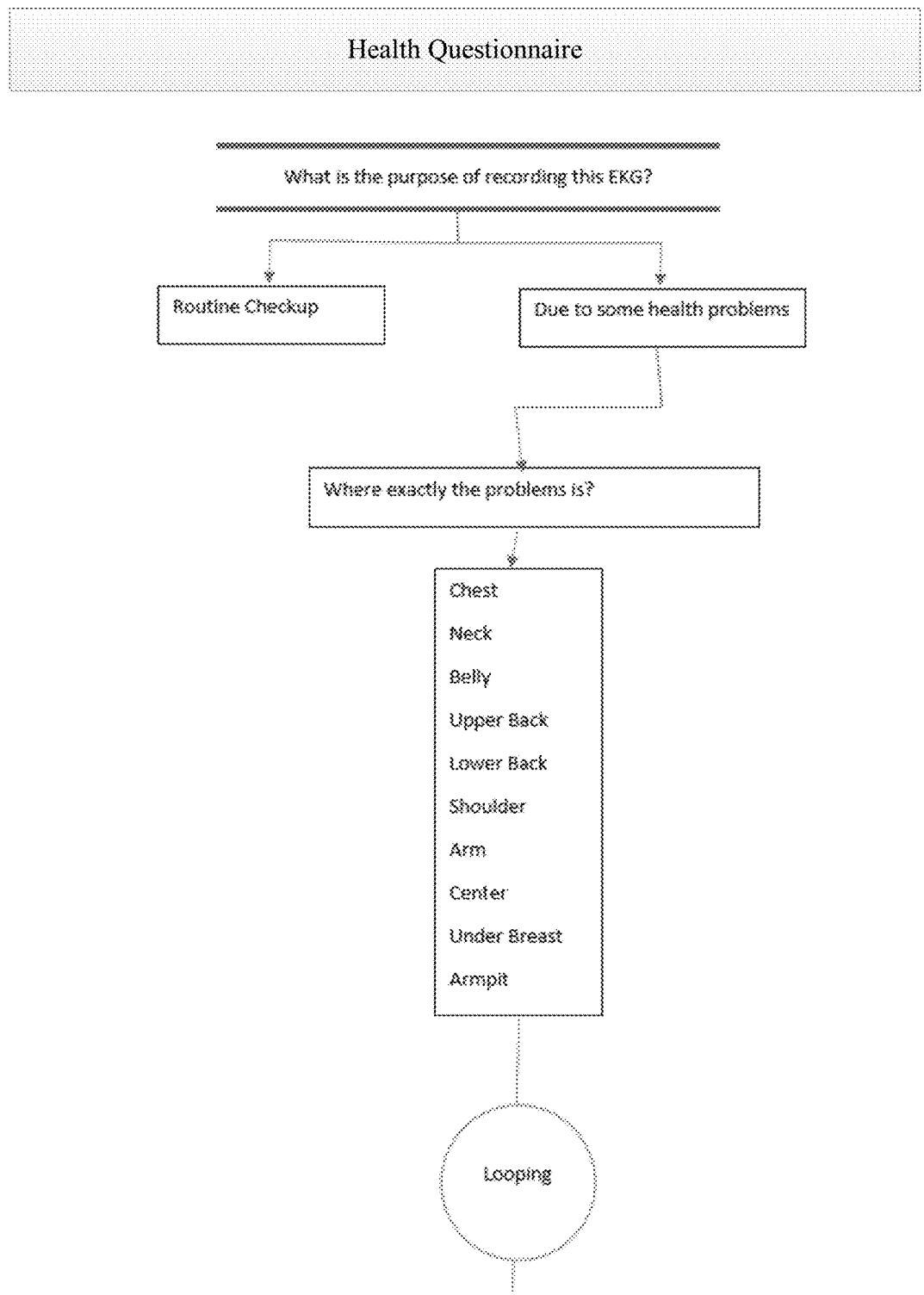
FIGS. 14A-14B illustrate an example flow of questions and answers that can be asked by the health questionnaire of the present disclosure.
Figure 14B:
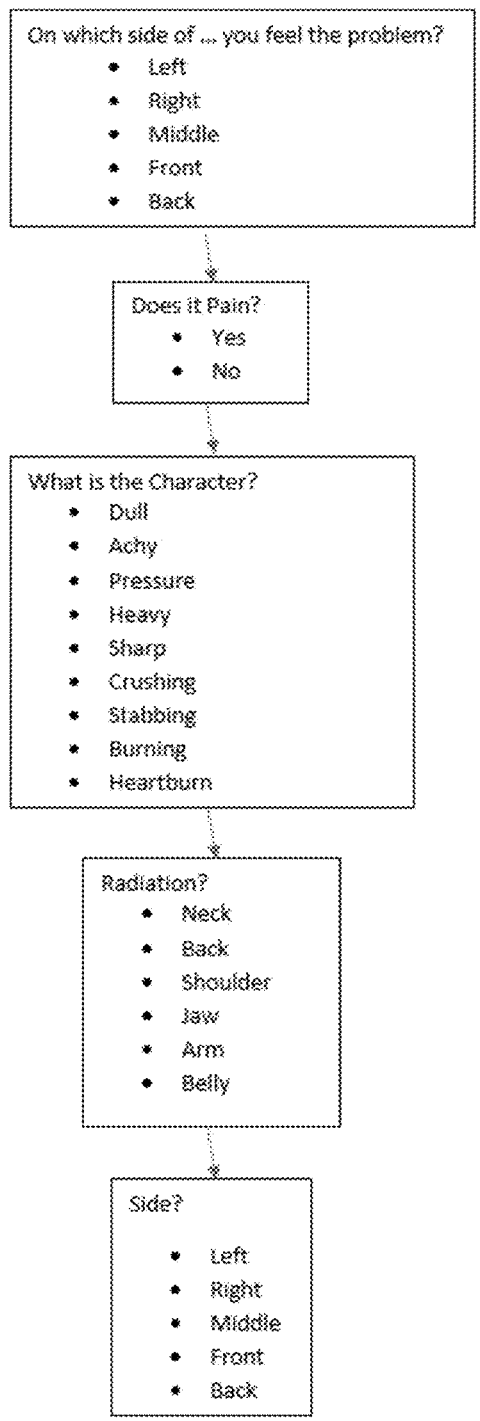

FIG. 13 is a flowchart illustrating process steps for answering a health questionnaire, carried out by the ECG application 46 of the present disclosure, indicated generally at 320. In step 322, the system 10 examines the user's authorization. For example, the system 10 may determine whether pre-conditions exist that would prevent the user from answering the questionnaire. The pre-conditions can include profile details being fully updated, the user assigning an appropriate role that tallows the user access to submit the health questionnaire (e.g., the user registered as a patient, not a physician), etc. In step 324, the system determines whether the user is authorized to answer the questionnaire. If the user in unauthorized, in step 326, the user device 14 displays an error message. If the user is authorized, in step 328, the user device 14 displays the questionnaire for user input. Once the questions are answered by the user, in step 330, the user selects a submit button. If the submission is unsuccessful, the system proceeds to step 332, where the user device 14 displays an error message. A submission can be unsuccessful when, for example, a questionnaire has been previously submitted. In such a case, the user can view the questionnaire in a read-only mode and can modify the answers by selecting a "Edit" button. If the submission is successful, the system proceeds to step 334, where the user device 14 displays a successful submission message. In step 336, the system stores the responses on the memory 24 and/or a cloud computing platform. In step 338, the system determines whether the system 10 stored or updated the responses. If an error occurred, in step 332, user device 14 displays an error message. If the system 10 stored or updated the responses successfully, the user device 14 proceeds to step 340, where the user device 14 displays a successful update message. FIGS. 14A and 14B show an example flow of questions and answers that can be asked by the questionnaire (carried out by the steps of 320 of FIG. 13).

Figure 15C:
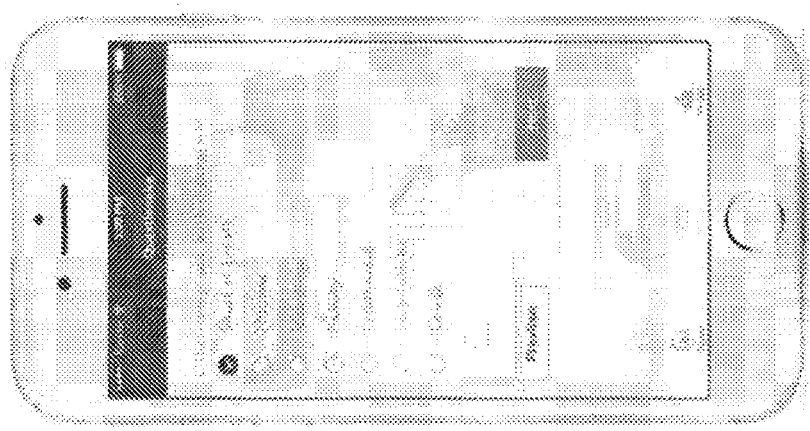
FIGS. 15A-15C are photos illustrating user interface screens generated by the user device including various health questionnaire screens.
Figure 15B:
Figure 15A:
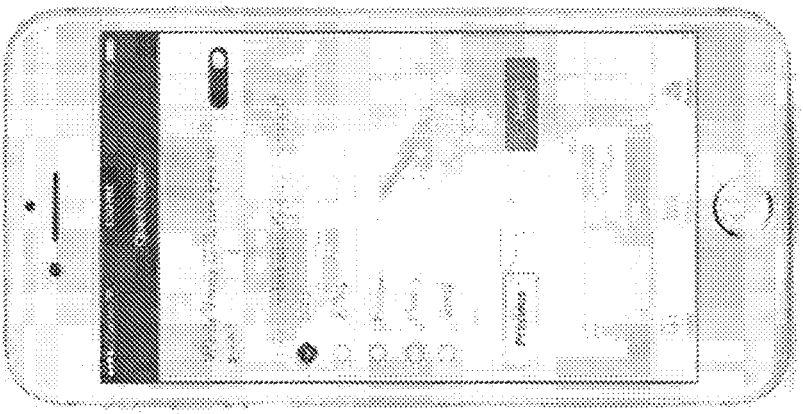
Figure 16B:
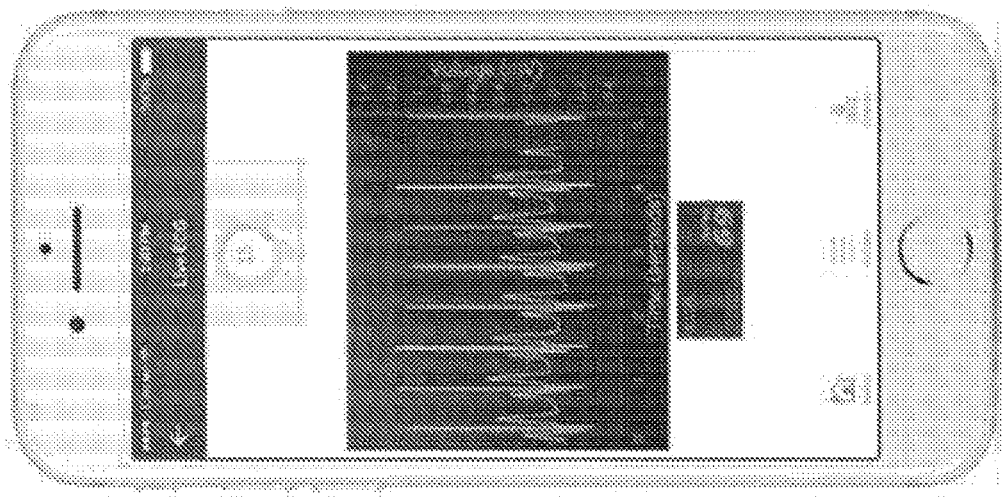
FIGS. 16A-16B are photos illustrating user interface screens generated by the user device including various health questionnaire screens.
Figure 16A:
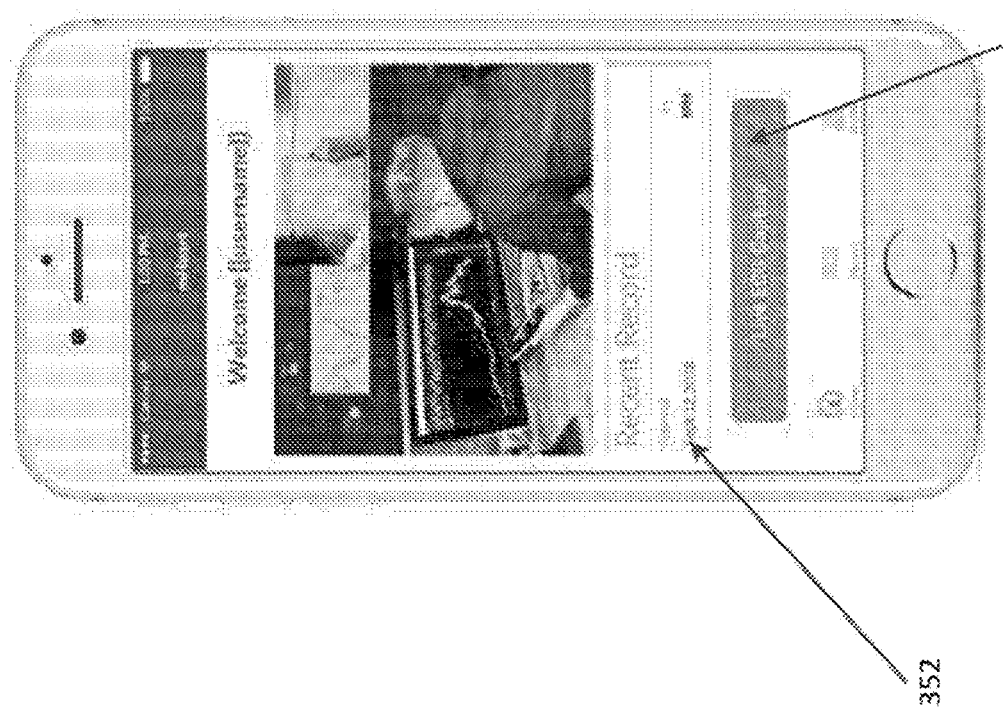

FIGS. 15A-15C illustrate example user interface screen of the ECG application 46, according to the present disclosure. Specifically, FIGS. 15A-15C show various questionnaire screens as discussed above in relation to FIG. 13. More specifically, FIG. 15A shows a first page of a health questionnaire, which asks the user if he/she is in pain, and, if yes, what are the pain's characteristics (following by a plurality of choices to answer the question). FIG. 15B shows a second page of the health questionnaire, which asks the user if the pain is relieved by one or more of a plurality of selectable answers, or if the pain is made worse by one or more of a plurality of selectable answers. FIG. 15C shows a third page of the health questionnaire, which asks the user if he/she has any other symptoms of discomfort, followed by a plurality of selectable answers, FIGS. 16A-16C illustrate user interface screen of an ECG capture, according to the present disclosure. Specifically, FIG. 16A shows the user is prompted with an ECG screen including a recent record button 352 (showing one ECG recording from Sep. 12, 2018) and a "Live ECG Capture" button 354. Selecting the recent record button 352 will display previously recorded ECG data or an ECG graph. It should be understood that the ECG recording from Sep. 12, 2018 is shown by way of example, and multiple ECG recordings from multiple dates and multiple times during a single date can be shown. Further, the user can filter ECG recordings by selecting specific or ranges of dates and times. The ECG recordings (and data) can be received and stored by the ECG application 46 from the ECG device 12, the server 20, a further device, an electronic transfer (e.g., air drop, text, email, Bluetooth connection, etc.), or from any other device or method.

Selecting the "Live ECG Capture" button 354 will display the screen shown in FIG. 16B. Specifically, FIG. 16B shows a live ECG graph (e.g., ECG signals in a wave form using a time series line chart) being generated from data received from the ECG device 12. Specifically, the ECG application 46 can receive single or multiple analog or digital signals from the ECG device 12, which are consolidated from multiple sensors (e.g., leads 18). It is noted that the user is connected to the ECG device 12 via the leads 18. The signal(s) can include raw data, consolidated data, formatted data, compressed data, converted data (e.g., ECG data plotted into a waveform), etc. Upon selection of the "Live ECG Capture" button 354, the ECG signals can be captured, transmitted and/or recorded immediately by the ECG device 12, after a predetermined delay, and/or for a predetermined duration, referred to hereafter as parameters. In a first example, the ECG signals can be captured between 5-25 seconds after selection of the button 354. In a second example, the ECG signals can be capture between 0-25 seconds after selection of the button 354, where the first 5 seconds are stored but not used for generating a waveform. The parameters can be set to any values by the user, a physician, a technician, etc., and can relate to industry standards or error mitigation techniques. As discussed above, the ECG data, ECG graph, or any other data generated from the ECG data can be stored on the ECG device 12, the user device 14, or the server 20.

Figure 17:
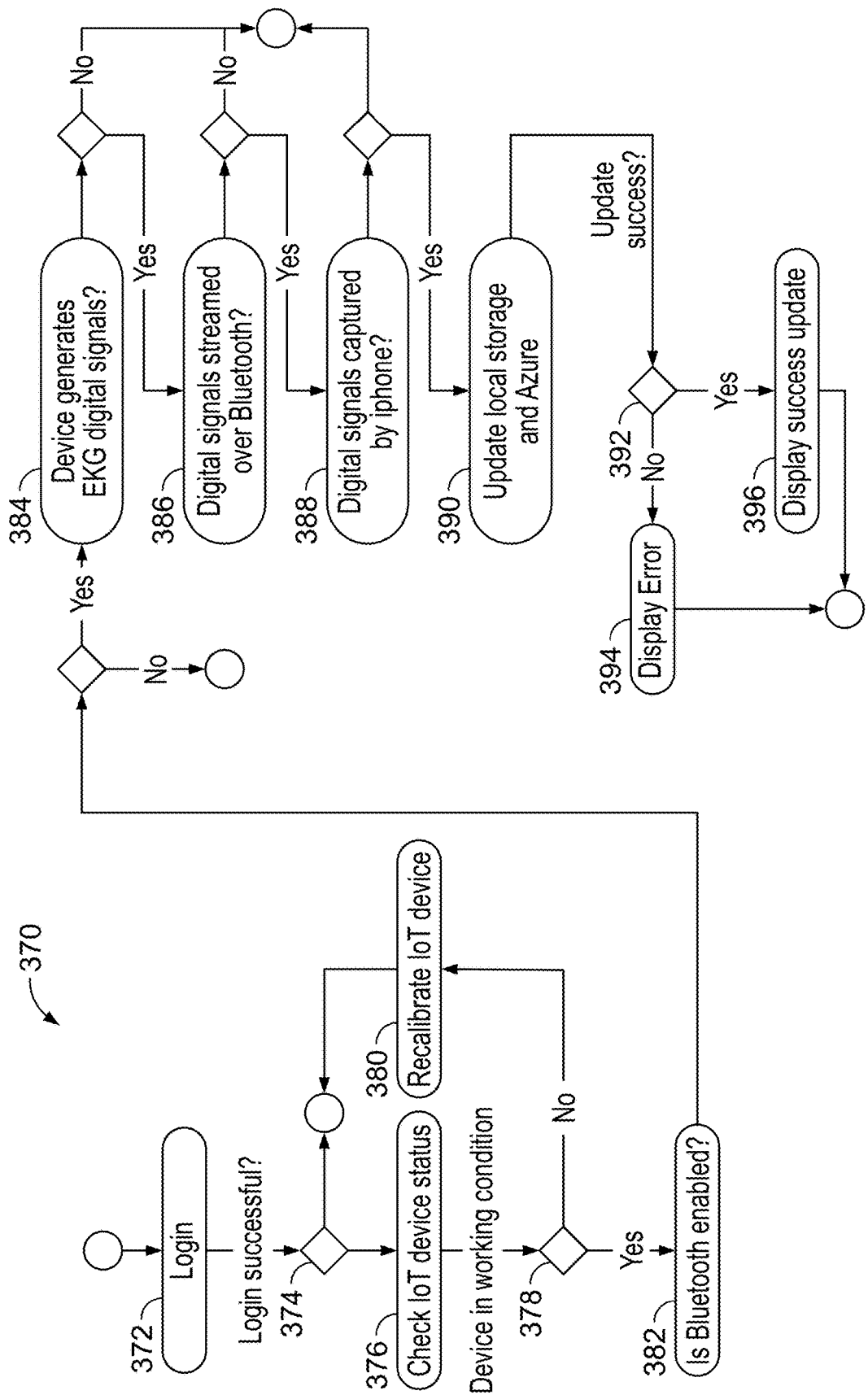
FIG. 17 is a flowchart illustrating process steps carried out by the user device of the present disclosure connecting with the ECG device.

FIG. 17 is a flowchart illustrating process steps for connecting with the ECG device 12, carried out by the ECG application 46 of the present disclosure, indicated generally at 370. In step 372, the user logs into the ECG application 46. In step 374, the system 10 determines whether the login was successful. If successful, in step 376, the ECG application 46 determines the status of the ECG device 12. In step 378, the ECG application 46 determines whether the ECG device 12 is in working condition. If the ECG device is not in working condition, in step 380, the system 10 transmits a signal to recalibrate the ECG device 12. If the ECG device 12 is in working condition, in step 382, the ECG application 46 determines whether the ECG device 12 and the user device 14 are synced via a Bluetooth connection (or any other wired or wireless connection). If the ECG device 12 and the user device 14 are synced, in step 384, the system 10 determines whether the ECG device 12 is generating ECG signals (digital and/or analog). If the ECG device 12 is generating ECG signals, in step 386, the system 10 determines whether the ECG signals are streaming over the Bluetooth connection. If the ECG signals are streaming over the Bluetooth connection, in step 388, the system 10 determines whether the ECG signals are being captured by the user device 14. If the ECG signals are captured by the user device 14, in step 390, the system 10 stores the ECG signals on the memory 44 and/or on the server 20. In step 392, the system 10 determines whether the ECG signals have been successfully stored. If the ECG signals have not been successfully stored (e.g., server unreachable, memory full, etc.), in step 394, the system 10 displays an error message on the user device 14. If the ECG signals have been successfully stored, in step 396, the system 10 displays an success message on the user device 14.

In an example, the ECG device 12 can connect directly to the network 16 via a LTE or WiFi connection, and comprise the ECG application 46. As would be understood by those skilled in the art, the ECG device 12 would be capable of performing the methods and function discussed above with regards to the user device 12. Thus, a need to pair the ECG device 12 to the user device 14 would be eliminated, as the ECG device 12 can perform the all of the combined functions of the ECG device 12 and the user device 14.

The system 10, via any or any combination of ECG device 12, the user device 14, and the server 20 can identify possible issues through a scoring algorithm or a risk score, such as, a low/medium/high risk or likelihood of having a cardiac condition, or other conditions. Additionally, critical values measured by the system 10 can be marked as low/medium/high risk. This can allow a user to determine whether to seek urgent medical attention. The scoring algorithms/risk scores can include a score involving platelet glycoprotein IIb/IIIa in unstable angina receptor suppression using Intergrilin (eptifibatide) therapy, a thrombolysis in myocardial infarction score, a global registry of acute coronary events score, a fast revascularization in instability in coronary disease score, a score related to heart history, ECG, age, risk factors and troponin, or any other suitable algorithm or risk score.

The system 10 can further provide advanced analytics and business intelligence solutions. For example, the system 10 can provide a visualization of data and information through dashboards, graphs, charts, visual key performance indicators ("KPI"), trends, etc. Further, the system can provide a cognitive and artificial intelligence platform capable of creating advanced machine learning algorithms to detect and identify trends, issues, predictions regarding the user's health status, utilizing proprietary and public domain algorithms (e.g., a stable chest pain assessment algorithm) with continuous learning capabilities, etc. The data and information can be stored in the server 20 or in the user device 14, and can be shared with medical personal, including, for example, hospitals, doctors, administrators, nurses, insurance agencies, etc. For example, a user can transmit the data and information to a doctor prior or during a checkup appointment.

Figure 18:
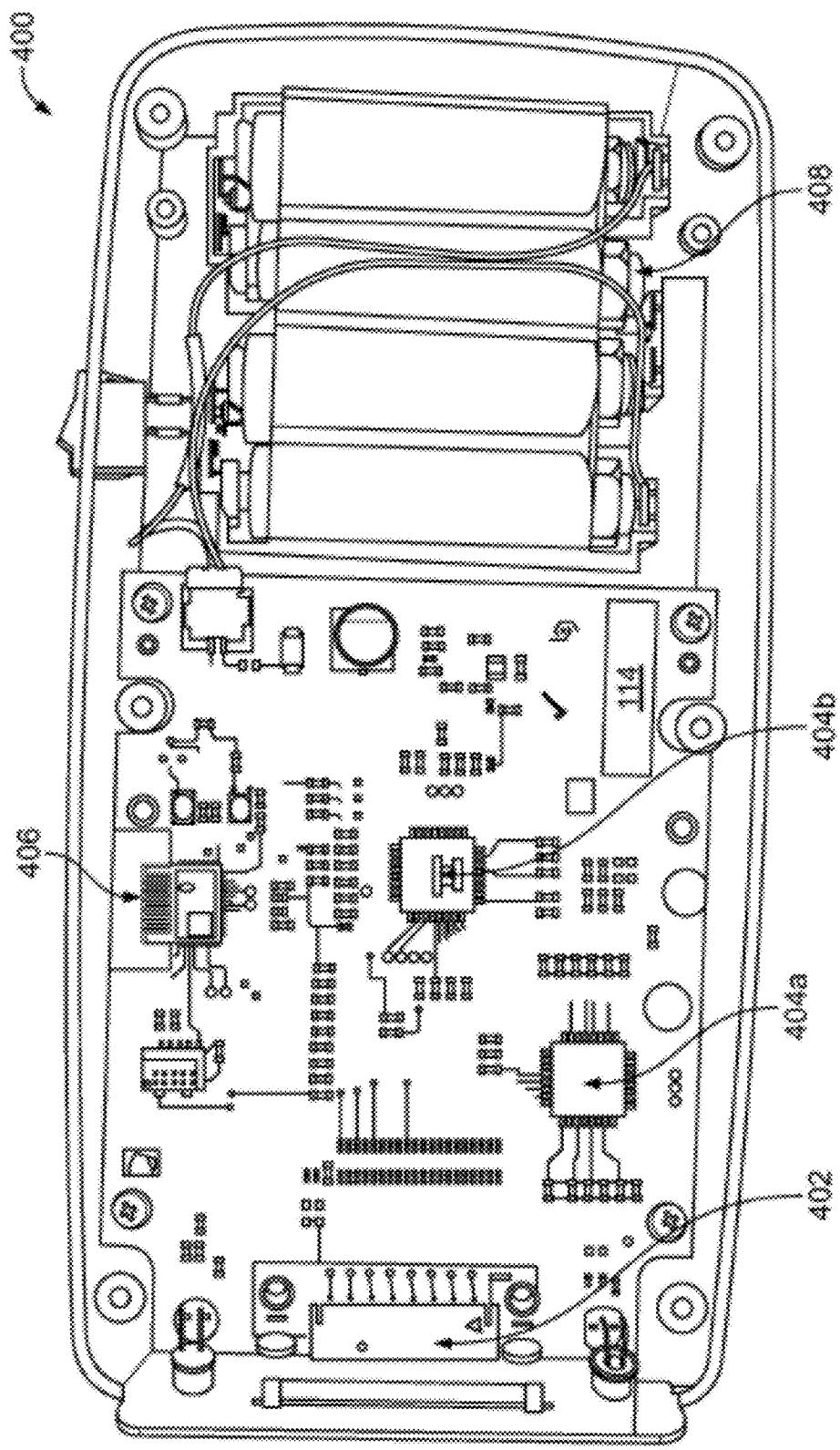
FIG. 18 is a photo illustrating a circuit board of an ECG device of the present disclosure.

FIG. 18 is a photo illustrating a circuit board of an ECG device 400. The ECG device 400 includes an ECG lead port 402, a pair of processors 404a and 404b, a Bluetooth transceiver 406, a battery pack 408, and other components. The ECG device 400 can connect to the user device 14 via a Bluetooth connection, and to a patient via an ECG lead system inserted into the ECG lead port 402.

Figure 19:
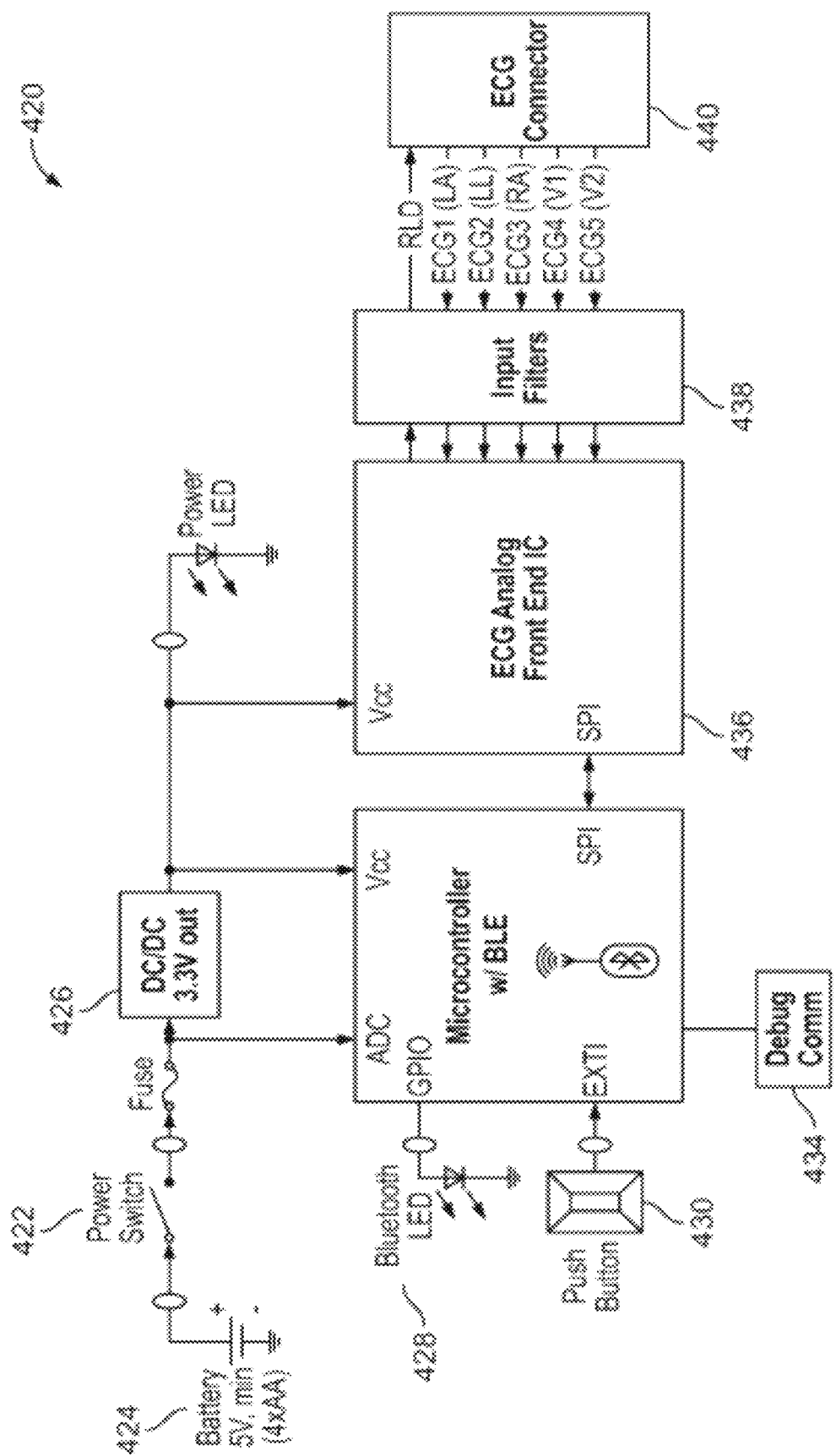
FIG. 19 s a block diagram showing an electrical schematic of an ECG device of the present disclosure.

FIG. 19 is a block diagram 420 of the ECG device of the present disclosure. It should be understood that the block diagram 420 is by way of example. The block diagram 420 includes a power switch 422, a battery 424, a DC/DC converter (3.3 V out) 426, a Bluetooth LED connectivity indicator 428, a push button 430, a microcontroller 432, a debugging communication port 434, an ECG analog front end integrated circuit 436, input filters 438, and an ECG connector 440.

Figure 20:
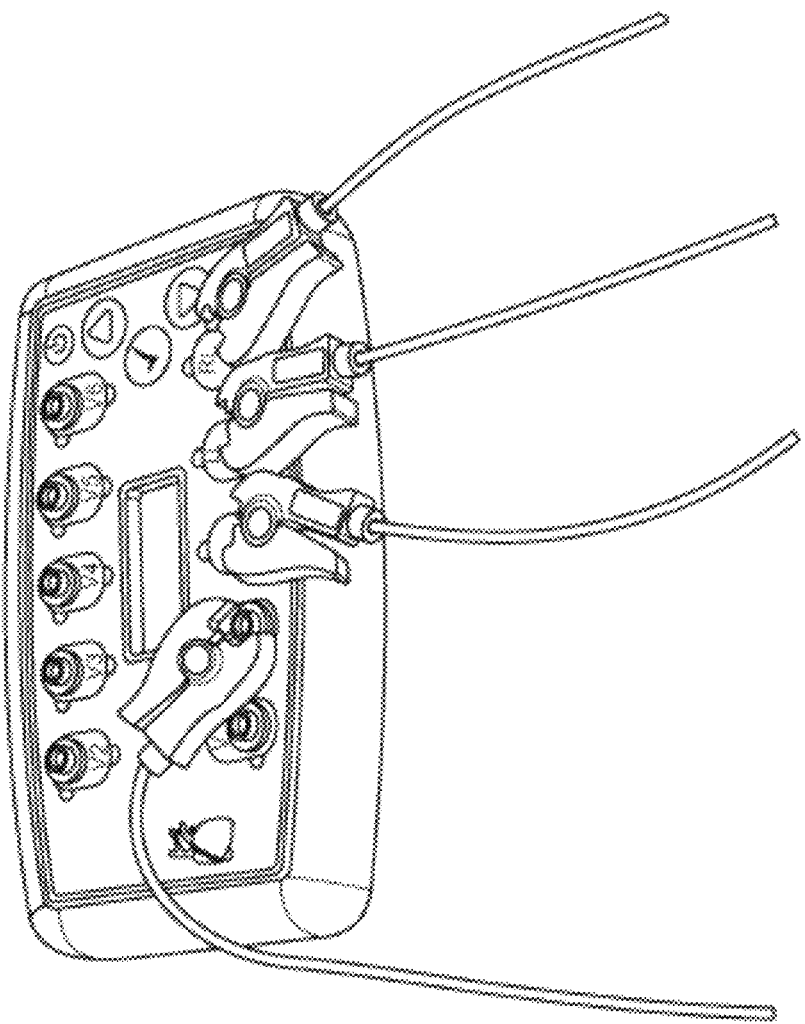
FIG. 20 is a photo of an ECG analog front end integrated circuit and an ADAS1000 evaluation board of the present disclosure.
Figure 20:
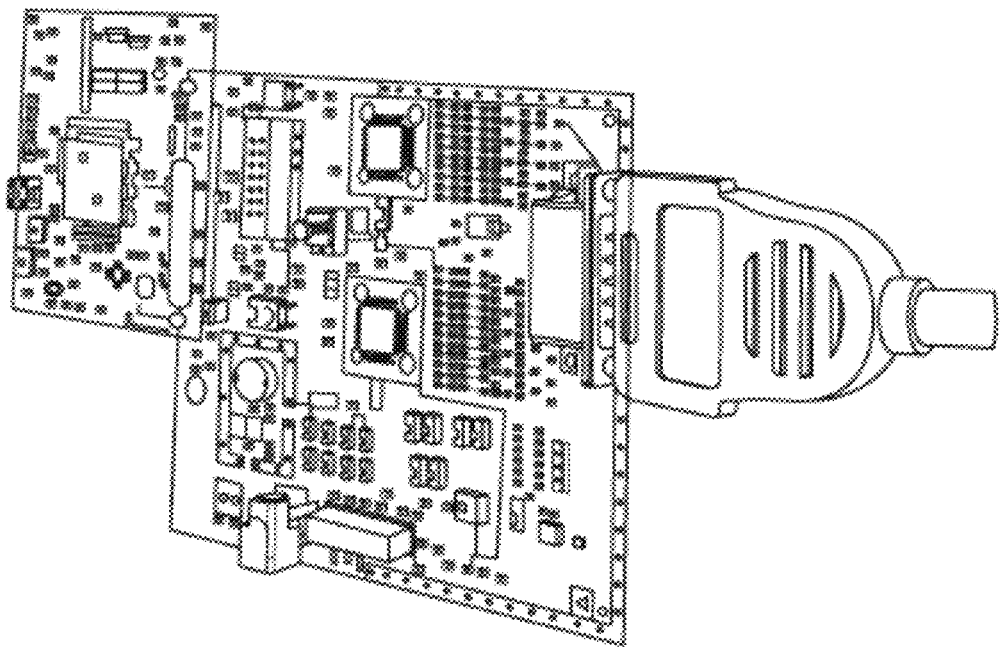

FIG. 20 is a photo of an ECG analog front end integrated circuit and an ADAS1000 evaluation board. The integrated circuit includes five acquisition ECG channels and one driven lead, can chain additional integrated circuits for 10+ channels, supports lead-off detection, internal pace detection, respiration detection via two electrodes, and includes a standard comm interface to microcontroller.

Figure 21:
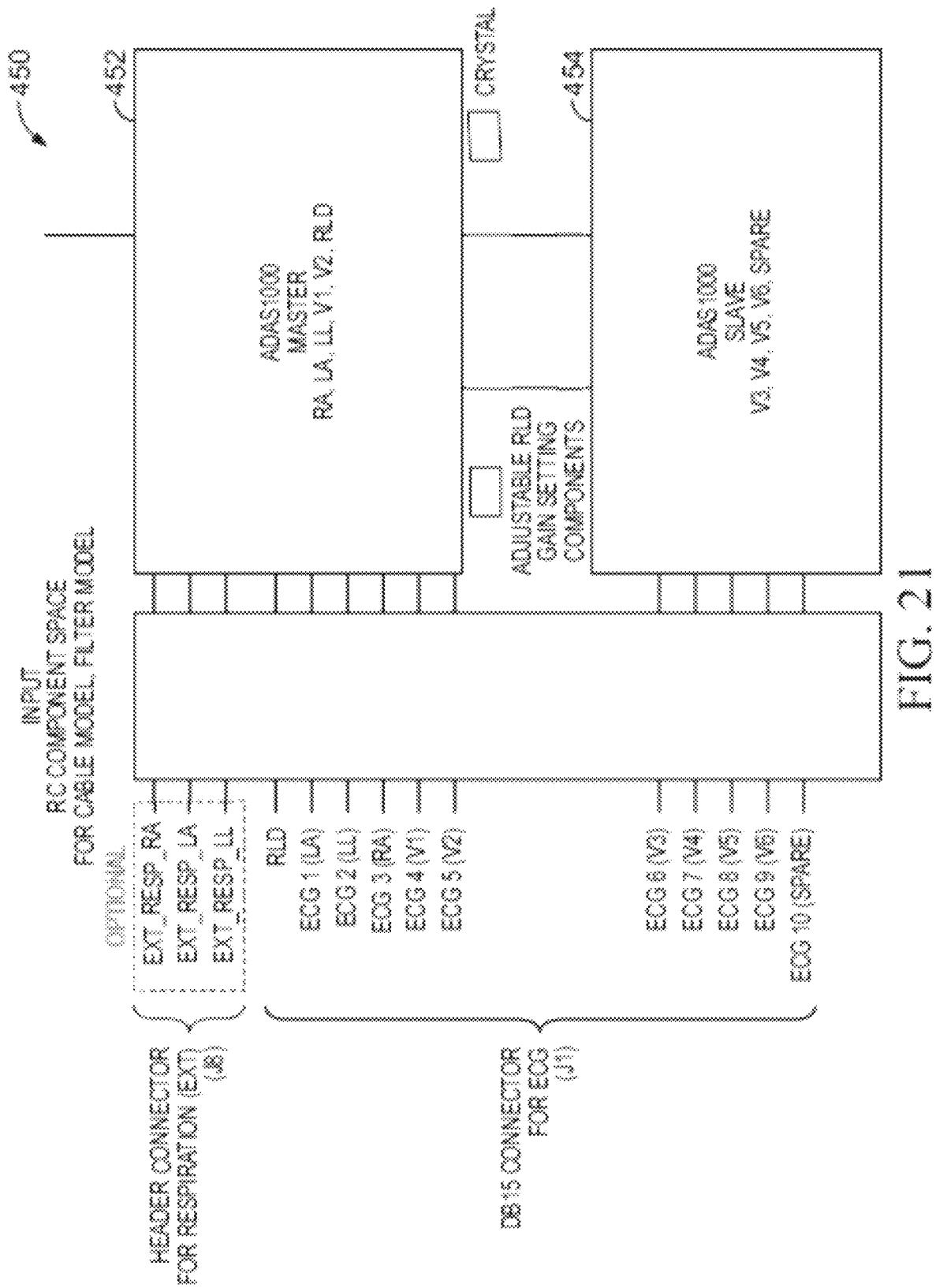
FIG. 21 is a block diagram showing an architecture of an ECG device of the present disclosure.

FIG. 21 is a block diagram 450 showing an architecture of an ECG device of the present disclosure. It should be understood that the block diagram 450 is by way of example. The master integrated circuit (ADAS1000) 452 can support six leads (four limbs+V1 and V2). The master integrated circuit 454 is connected to a slave integrated circuit 454 to support up to 12 leads (including V3, V4, V5, V5, Spare).

Figure 22:
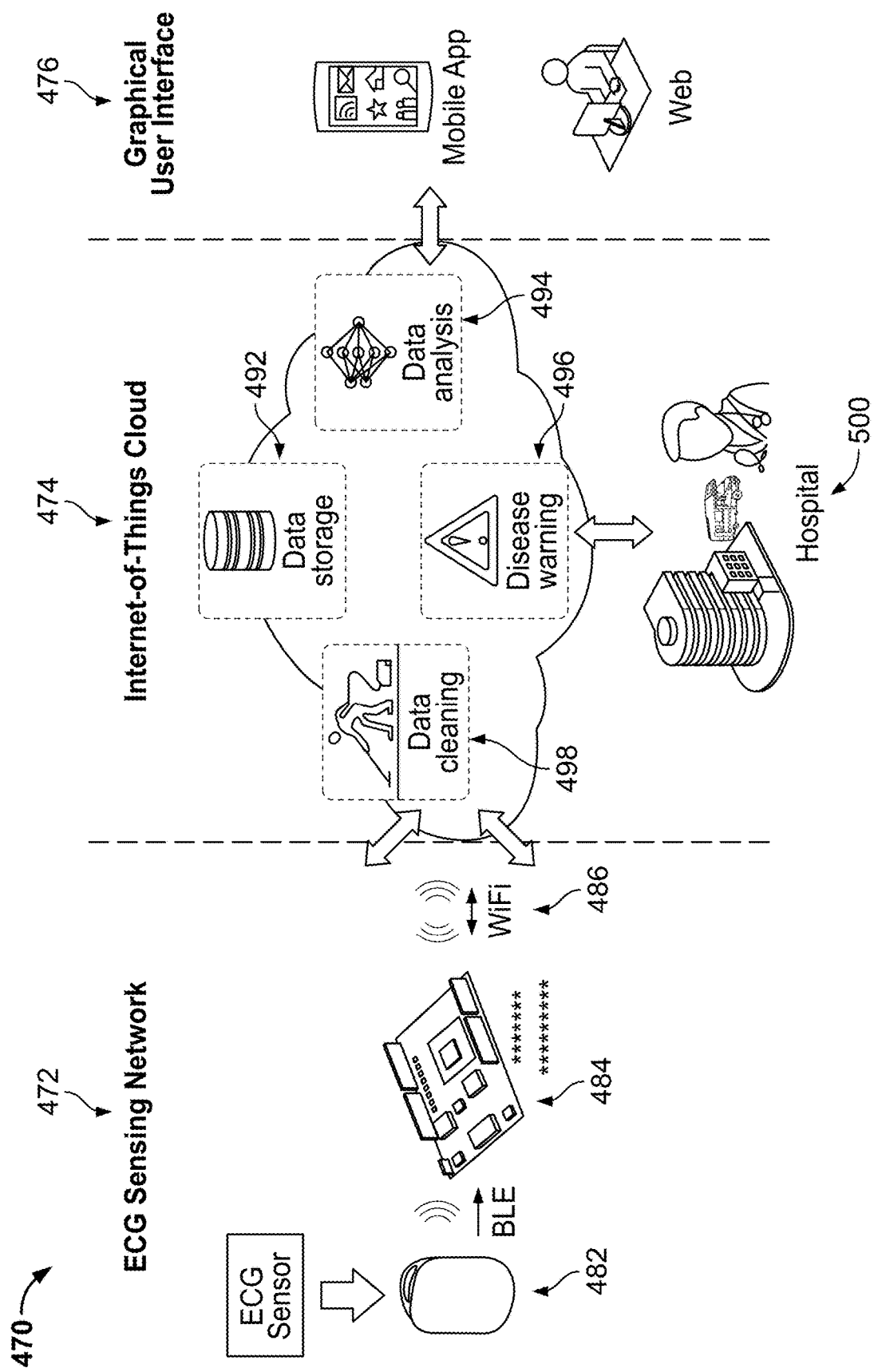
FIG. 22 is a diagram illustrating an IoT-based ECG monitoring system of the present disclosure.
Figure 23:
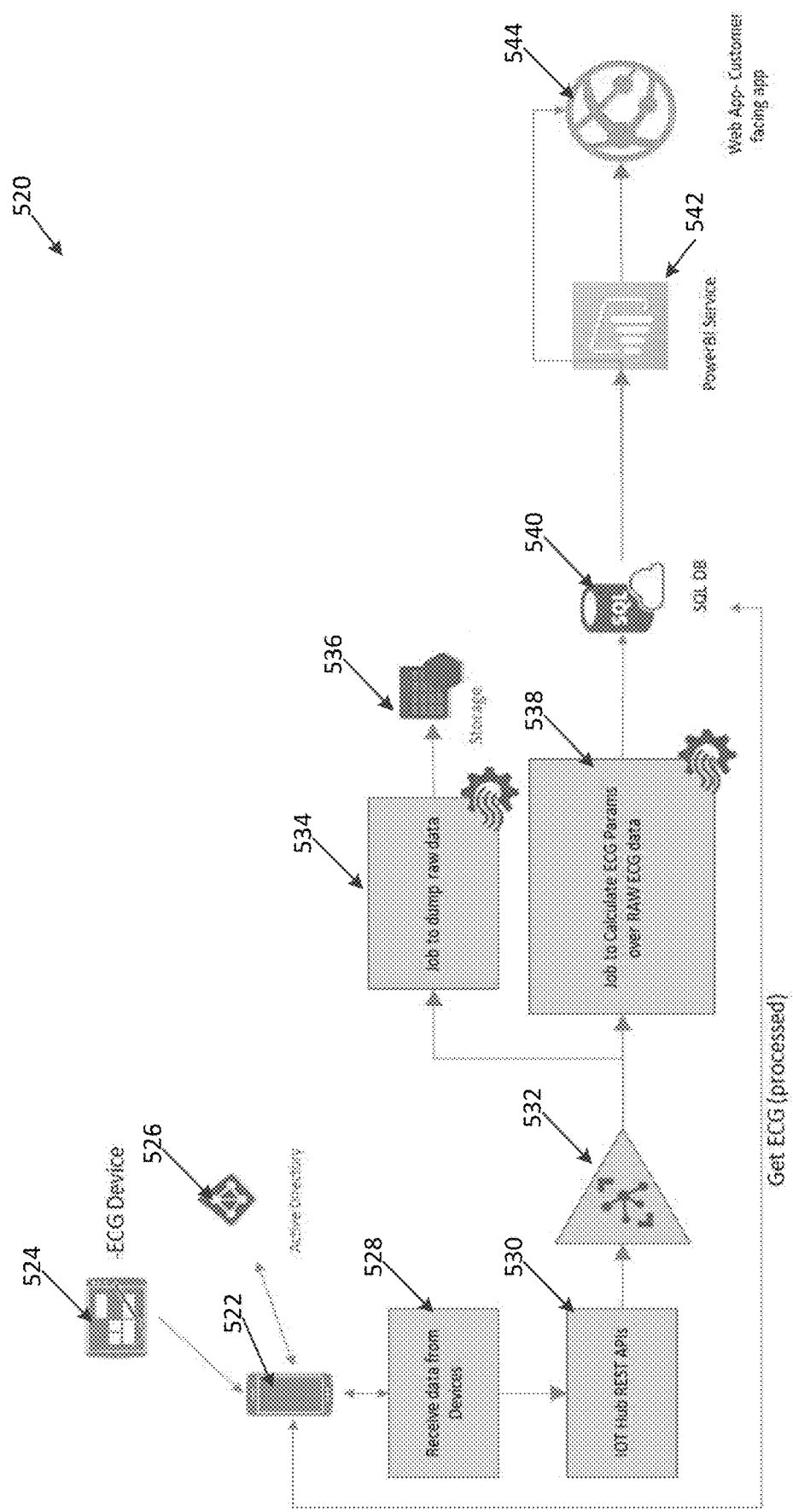
FIG. 23 is a diagram showing system functions of the IoT-based ECG monitoring system of FIG. 22 of the present disclosure.

FIG. 22 is a diagram illustrating an IoT-based ECG monitoring system in accordance with the present disclosure, indicated generally at 470. The system includes an ECG sensing network 472, the IoT cloud platform 474, and the graphical user interface 476. The ECG system 470 establishes a bridge between the digital world (e.g., the internet) and the real word (e.g., a physical device, such as the user device 14, where physical devices are connected to a cloud platform and create a unique identification over the Internet in the cloud platform. The ECG sensing network 472 includes an ECG sensor 482 connected via a wireless connection (e.g., a Bluetooth connection) to a network capable device 484, which is connected via a wireless connection (e.g., a WiFi connection) to the IoT cloud 474. The ECG sensor 482 can be the lead 18, the ECG device 12, or any other ECG sensor device. The network capable device 484 can be the ECG device 12, the user device 14, or any other device capable of connecting to the Internet.

The IoT cloud 474 platform includes data storage system 492, a data analysis system 494, a disease warning system 496, and a data cleaning system 498. The data storage system 492 can be any type of storage system, including, but not limited to the server 20. For example, the data storage 492 can include a Cosmos database, which is a cost-effective service that stores the data that IoT devices send to the cloud. The database stores large meter data and supports flexible data format to derive insights, and follows semi-structured model to easily combine various device types having differing data schemes.

The data analytics system 494 can be any type of analytics system, such as those discussed in the present disclosure regarding analyzing ECG data. For example, the data analysis system 494 can include use a real-time analytics service, such as Stream Analytics, to help in the detection of anomalies and retrieval of archived data from smart meters/devices. The analytics service allows to write stream processing logic in a language similar to SQL from the data derived from the connected devices and forwards the extracted results to the event hub, a business analytics service (e.g., Power BI) and table storage services The disease warning system 496 can be any type of system to warn a user or medical professional of a disease risk to the user (e.g., a low/medium/high risk or likelihood of having a cardiac condition, etc.) The data cleaning system 498 can be any type of system to detect and correct (or remove) corrupt or inaccurate records from a record set, a table, a dataset, etc. The IoT cloud 474 can communicate wirelessly with medical professionals 500 or with the graphical user interface 476, which includes a mobile app 502 (e.g., ECG application 46 or any other mobile app) and the Internet 504 (e.g., a website, a web app, etc.). The web apps and mobile apps, part of app service, help in hosting a web application used for configuring and sending commands to devices (e.g., the ECG device 12, the user device 14, the leads 18,), inspecting the data dashboard, creating or updating business logic and perform several events-driven functions.

It is noted that the IoT-based ECG monitoring system 470 can be categorized into six layers, which include smart device and controllers (e.g., ECG sensors), connectivity and protocol communication, an IoT hub, a cloud server, data storage and accumulation, data analysis and computing, and user applications and report generation. The IoT hub is a key component of any IoT solution. It primarily serves as a cloud gateway that connects all the ECG devices with the cloud and establishes communication between them. It can scale to connect millions of meters and can process huge volumes of data. It supports multiple protocols such as http, AMPG, MQTT to enable control and command capabilities. It is also responsible for per-device authentication, thus playing a major role in security aspects. The IoT hub also provides secure communication between ECG and user devices, and the cloud platform. Other systems that can be used include a message broker, used to connect systems and receive messages, and a rules engine(s), which can processes messages and provide an intergration mechanism with other services/systems, such as the databases.

The IoT-based ECG monitoring system 470 can include an event hub, which handles millions of events every second to stream the events into various applications. Variable load profiles like connected devices, mobile apps, application performance counters generate telemetry data periodically and/or in real time. The event hub consumes these events to accommodate numerous load profiles and process massive amounts of data The IoT-based ECG monitoring system 470 can further enable transformation of collected data into intelligence using, for example, a machine learning system (e.g., Azure ML, etc.). The machine learning system offers limitless scalability, availability and unmatched security. Also, the machine learning system generates powerful insights for real-time and predictive analytics, helps in fixing resilient & persistent issues, and makes reliable predictions, which can help the utility operations team and the consumers to become aware of utility usage.

FIG. 22 is a diagram showing system functions of the IoT-based ECG monitoring system 470, indicated generally at 520. The user device 522 can receive data (e.g., ECG data) from the ECG device 524, and communicate with an active directory system 526, which can provide a platform with enhanced security, access management, scalability and reliability for connecting users with applications. In function 528, the system 470 receives data from devices (e.g., the user device 522), and transmits the data an IoT hub REST API(s) 530. Next, the system 470 transmits the data to a cloud gateway 532, which can dump raw data 534 onto a storage server 536, and calculate ECG params over the raw ECG data 538. The ECG params can be transmitted to a SQL database 540. In addition, the SQL database 540 can communicate directly with the user device 522. The system can further transmit data from the SQL database to a business analytic service 542 (e.g., PowerBI), which can transmit processed data to a web or mobile application 544 for display.

The following additional analysis information is provided to further highlight the benefits and advantages of the ECG system of the present disclosure.

Political: The political climate has been dictating cheaper and faster care with a reduction in cost, length of stay, and readmissions. Medical care spending comprises nearly 18% of the US GDP.

The Affordable Care Act (ACA) continues to be an economic burden and may become unsustainable. Recent projections by the Congressional Budget Office expect the majority of individuals enrolled in an insurance program to be those in the Medicaid pool, whereas private insurance enrollments will decrease. This raises a concern as to the sustainability of the ACA. Current politicians are looking to amend the ACA in order to reduce costs and provide a modified bill which meets the short-term and long-term needs of the American people without bankrupting the country.

Economic: According to the Institute for New Economic Thinking, the ACA's expenses are skewed such that the sickest 10% of the patients utilize nearly ⅔ of every healthcare dollar. The cost per person (of the sickest patient) is approximately 54,000/yr. The remaining 90% of the patients cost an average of 6000/yr.

The ECG system offers a low cost solution to help reduce the number of ER visits for all chest pain patients, and especially those who have had a prior cardiac issue.

Societal: At a biomedical level, the ECG system offers data very similar to a traditional 12-lead ECG. However, correlation through clinical trials is needed to validate the data. Society's challenge is accepting proof of concept that a system capable of learning symptoms, risk factors, physical exam, and ECG data provides feedback as an adjunct to that of a clinician.

Other societal benefits come from fewer days lost from work and less stress on patient support systems such as friends/family.

Societal challenge: clinical risk through poor performance
Mitigate by rigorous clinical quality control.
Chest pain lasting more than 10 min, with typical symptoms will instruct the patient to call Emergency Services.

Technological: As with any mobile health platform, cybersecurity and patient privacy are of concern.

The data obtained from each patient must be scrutinized carefully as it will be a skewed/biased population based on disease state or disease concern. Improvements in algorithmic assessments should be based on scientifically validated and accepted data.

Currently, the European Union and the Food and Drug Administration (FDA) are actively working on policies and procedures to regulate new mobile health technology. Currently the FDA grants device approvals via a 510(k) pathway. This pathway allows new technology to prove equivalence to pre-existing technology.

Environmental: By reducing patient visits to the ER, with a downstream effect of reducing admissions, there will be a reduction in energy consumption as well as waste. The ECG system not only has a direct impact on the environment, but the long term effect of a cleaner environment is a healthier community.

T-M-O Analysis: As a new player in the wearables market, the ECG system's niche for exploitation is the diagnostic algorithm space integrated with risk stratification to assist in the triage process.

Currently, the only ECG monitoring devices available for mobile use are single-lead systems for the lay person which are able to evaluate heart rhythms and 2-3-lead systems which are intended for physicians to prescribe for use on patients for the purpose of arrhythmia detection.

Today, a 9-lead system with an app designed to help provide triage-related advice does not exist. The ECG system, at this time, is the initial company in this segment of the wearables market, thereby giving it a first mover advantage.

Early competitors include Cardionet, LifeWatch®, Cardiostaff, Medtronic, and AMI-cardiac monitoring. All of these systems are 2-3-channel systems and monitor for arrhythmias only with the exception of LifeWatch® which performs ST segment monitoring as well. Qardio and Omron arrhythmia monitors are designed for the layperson coupled with a mobile app and are single lead systems only. The Omron system is not a wearable

Having thus described the system and method in detail, it is to be understood that the foregoing description is not intended to limit the spirit or scope thereof. It will be understood that the embodiments of the present disclosure described herein are merely exemplary and that a person skilled in the art may make any variations and modification without departing from the spirit and scope of the disclosure. All such variations and modifications, including those discussed above, are intended to be included within the scope of the disclosure. What is intended to be protected by Letters Patent is set forth in the following claims.

What is claimed is:

1. A method for operating a mobile electrocardiogram ("ECG") system, the method comprising:
providing a wearable object with an integrated lead system;
receiving, by a portable ECG device, ECG signals from the lead system of the wearable object being worn by a user;
recording, by the portable ECG device, first ECG data of a user based on the received ECG signals;
transmitting, from the portable ECG device, the ECG data for the user to a user device and/or a remote datastore;
receiving, by a processor, a request to perform a health analysis made by a user via a user-software interaction with a user device;
receiving, by the processor from the user device, responses to a plurality of questions associated with a current health status of the user;
receiving, by the processor from the remote data store, the first ECG data of the user which was previously recorded;
receiving, by the processor via the portable ECG device, current second ECG data of the user;
comparing the first ECG data of the user and the current second ECG data of the user to differentiate between cardiac chest pain and non-cardiac chest pain;
determining, based on the comparing and the received responses, a risk level from a plurality of different levels of risk of a cardiac event;
controlling operations of the user device to output a recommendation whether or not the user should visit an emergency room (ER) based on the risk level which was determined;
automatically changing one or more parameter settings of the portable ECG device based on the risk of the cardiac event; and
monitoring, by the portable ECG device, a respiratory rate via the lead system of the wearable object from which the ECG signals were previously received;
wherein the wearable object comprises a chest and abdomen plate with the lead system incorporated therein.

2. The method of claim 1, further comprising transmitting the current second ECG data, via a transceiver of the portable ECG device, to at least one of the user device or a cloud-based storage system, wherein the transceiver is one of a cellular transceiver, a Bluetooth transceiver or a WiFi transceiver.

3. The method of claim 2, wherein the step of transmitting the current second ECG data is in response to a request from the user device.

4. The method of claim 1, wherein the portable ECG device comprises a lead system that comprises 8 leads producing a 10 channel output.

5. The method of claim 4, wherein the lead system is expandable to a 12 channel output.

6. The method of claim 1, wherein the portable ECG device comprises a lead system that comprises 10 leads producing a 12 channel output.

7. The method of claim 1, wherein determining, based on the comparison and the received responses, the risk of the cardiac event comprises using a score.

8. The method of claim 7, wherein the score comprises a thrombolysis in myocardial infarction (TIMI) score.

9. The method of claim 7, wherein the score comprises using a global registry of acute coronary events score, a fast revascularization in instability in coronary disease score, or a score related to heart history, age, risk factors, weight, medical history, prior symptoms, or sex of the user.

10. The method of claim 9, wherein determining the risk of the cardiac event comprises using a thrombolysis in myocardial infarction (TIMI) scoring algorithm.

11. The method of claim 1, wherein the portable ECG device comprises a lead system that comprises a chest patch, a first wrist bracelet, a second wrist bracelet, a first ankle bracelet, and a second ankle bracelet.

12. The method of claim 1, wherein receiving, via the portable ECG device, the current second ECG data of the user comprises capturing ECG signals via one or more leads of a lead system included in the portable ECG device, the one or more leads having an electrode at a first end thereof and an electrical connection to an ECG lead port of the portable ECG device at a second end thereof.

13. The method of claim 1, further comprising receiving oxygen saturation data of the user from an oxygen sensor included in the portable ECG device.

14. The method of claim 13, further comprising receiving body temperature data of the user from a temperature sensor included in the portable ECG device.

15. The method of claim 13, further comprising receiving rate of respiration data of the user from a respirometer included in the portable ECG device.

16. The method of claim 13, further comprising receiving body temperature data of the user from a temperature sensor included in the portable ECG device and receiving rate of respiration data of the user from a respirometer included in the portable ECG device.

17. The method of claim 1, further comprising receiving body temperature data of the user from a temperature sensor included in the portable ECG device.

18. The method of claim 1, further comprising receiving rate of respiration data of the user from a respirometer included in the portable ECG device.

19. The method of claim 1, further comprising determining, based on the comparison and the received responses, the likelihood of a non-cardiac medical condition.

20. The method according to claim 1, wherein the wearable object comprises a wearable clothing item.

21. The method according to claim 1, wherein the chest or abdomen plate comprises chest patches with adjustable components for body sizing and location placement.

22. The method according to claim 1, wherein the one or more parameter setting comprises a parameter setting for a display.

* * * * *